United States Patent
Evans

(10) Patent No.: US 6,670,127 B2
(45) Date of Patent: Dec. 30, 2003

(54) METHOD FOR ASSEMBLY OF A POLYNUCLEOTIDE ENCODING A TARGET POLYPEPTIDE

(75) Inventor: Glen A. Evans, San Marcos, CA (US)

(73) Assignee: Egea Biosciences, Inc., San Diego, CA (US)

(*) Notice: Subject to any disclaimer, the term of this patent is extended or adjusted under 35 U.S.C. 154(b) by 0 days.

(21) Appl. No.: 09/922,221

(22) Filed: Aug. 2, 2001

(65) Prior Publication Data

US 2003/0087238 A1 May 8, 2003

Related U.S. Application Data

(63) Continuation-in-part of application No. 09/554,929, filed as application No. PCT/US98/19312 on Sep. 16, 1998.
(60) Provisional application No. 60/059,017, filed on Sep. 16, 1997.

(51) Int. Cl.[7] .............. C12Q 1/68; C12P 19/34; C07H 21/00; C07H 21/02; C07H 21/04
(52) U.S. Cl. .............. 435/6; 435/91.1; 435/91.2; 536/25.3
(58) Field of Search .............. 435/6, 91.1, 91.2; 536/25.3

(56) References Cited

U.S. PATENT DOCUMENTS

| | | | |
|---|---|---|---|
| 4,652,639 A | 3/1987 | Stabinsky | 536/27 |
| 5,198,346 A | 3/1993 | Ladner et al. | 435/69.1 |
| 5,387,756 A | 2/1995 | Burrell et al. | 800/205 |
| 5,723,323 A | 3/1998 | Kauffman et al. | 435/172.3 |
| 5,763,192 A | 6/1998 | Kauffman et al. | 435/7.1 |
| 5,814,476 A | 9/1998 | Kauffman et al. | 435/69.1 |
| 5,817,483 A | 10/1998 | Kauffman et al. | 435/69.1 |
| 5,824,514 A | 10/1998 | Kauffman et al. | 435/91.1 |
| 5,922,927 A | 7/1999 | Bujard et al. | 800/25 |
| 5,925,538 A | 7/1999 | Perkins et al. | 435/66 |
| 5,935,527 A | 8/1999 | Andrus et al. | 422/131 |
| 5,942,609 A | 8/1999 | Hunkapiller et al. | 536/25.3 |
| 5,968,799 A | 10/1999 | Gelfand et al. | 435/194 |
| 5,976,862 A | 11/1999 | Kauffman et al. | 435/252.3 |
| 5,981,601 A | 11/1999 | Nagley et al. | 514/690 |
| 6,083,726 A | 7/2000 | Mills, Jr. et al. | 435/91.1 |
| 6,087,100 A | 7/2000 | Meade et al. | 435/6 |
| 6,110,457 A | 8/2000 | Belshe et al. | 424/93.2 |
| 6,110,668 A | 8/2000 | Strizhov et al. | 435/6 |
| 6,159,687 A | 12/2000 | Vind | 435/6 |
| 6,175,006 B1 | 1/2001 | Andrus et al. | 536/25.4 |
| 6,274,353 B1 | 8/2001 | Yang | 435/91.2 |

FOREIGN PATENT DOCUMENTS

| | | |
|---|---|---|
| EP | 0 316 018 | 2/1986 |
| EP | 0 385 410 | 2/1990 |
| WO | WO 9000626 | 1/1990 |
| WO | WO 9412632 | 6/1994 |
| WO | WO 01/00816 | 1/2001 |

OTHER PUBLICATIONS

Agarwal et al., "Synthesis, cloning and expression of a synthetic gene for high potential iron protein from *chromatium vinosum*," Biochem. Biophys. Res. Commun., 197 (3):1357–1362 (1993).

Ashman et al., "Chemical synthesis, expression and product assessment of a gene coding for biologically active human tumor necrosis factor alpha," *Protein Eng.*, 2(5):387–391 (1989).

Bell et al., "Chemical synthesis cloning and expression in mammalian cells of a gene coding for human tissue–type plasminogenactivator" *Gene*, 63:155–163 (1988).

Bergmann et al., "Chemical synthesis and expression of a gene coding for hirudin, the thrombin–specific inhibitor from the leech *hirudo medicinalis*," *Biol. Chem. Hoppe, Seyler.*, 367(8) :731–740 (1968).

Biernat et al., "The construction and cloning of synthetic genes coding for artificial proteins and expression studies to obtain fusion proteins," *Protein Eng.*, 1(4) :345–351 (1987).

Calogero et al., "Chemical synthesis and in vivo hyperexpresion of a modular gene coding for *Escherichia coli* translational initiation factor IFI," *Mol. Gen. Genet.*, 208:63–69 (1987).

Chalmers and Curnow, "Scaling up the ligase chain reaction–based approach to gene synthesis," *Biotechniques*, 30(2):249–252 (2001).

Ciccarelli et al., "Construction of synthetic genes using PCR after automated DNA synthesis of their entire top and bottom strands," *Nucleic Acids. Res.*, 19 (21) :6007–6013 (1991).

Cravador et al., "Total DNA synthesis and cloning in *Escherichia coli* of a gene coding for the human growth hormone releasing factor," *Biochimie.*, 67:829–834 (1985).

Danilyuk et al., "Effective synthesis and cloning of the gene of human interleukin–2 gene and an analog of it: expression of the interleukin–2 gene in E. coli cells," *Bioorg. Chem.*, 17 (6):446–454 (1991).

(List continued on next page.)

Primary Examiner—Ethan Whisenant
Assistant Examiner—Arun Kr. Chakrabarti
(74) Attorney, Agent, or Firm—McDermott, Will & Emery

(57) ABSTRACT

The present invention provides a novel approach to utilizing the results of genomic sequence information by computer–directed polynucleotide assembly based upon information available in databases such as the human genome database. Specifically, the present invention can be used to select, synthesize and assemble a novel, synthetic target polynucleotide sequence encoding a target polypeptide. The target polynucleotide can encode a target polypeptide that exhibits enhanced or altered biological activity as compared to a model polypeptide encoded by a natural (wild-type) or model polynucleotide sequence.

23 Claims, 18 Drawing Sheets

OTHER PUBLICATIONS

Denèfle et al., "Chemical synthesis of a gene coding for human angiogenin, its expression in *Escherichia coli* and conversion of the product into its active form," *Gene*, 56:61–70 (1987).

Dillon et al., "A rapid method for the construction of synthetic genes using the polymerase chain reaction," *Biotechniques*, 9(3):298–300 (1990).

Dobrynin et al., "Chemical–enzymatic synthesis and cloning of DNA, coding the signal for secretion of proteins in gram–negative bacteria," *Bioorg. Chem.*, 15(9):684–690 (1989).

Dobrynin, et al., "Synthesis of a model promoter for a gene expression in *Escherichia coli*," *Nucleic Acids Synp. Ser.*, 7:365–376 (1980).

Edge et al., "Total synthesis of a human leukocyte interferon gene," *Nature*, 292:756–762 (1981).

Eidsness et al., "Expression of synthetic gene coding for the amino acid sequence of *clostridium pasteurianum* rubredoxin," *Protein Eng.*, 5(4):367–371 (1992).

Eren and Swenson, "Chemical synthesis and expression of a synthetic gene for the flavodoxin from *clostridium MP*," *J. Biol. Chem.*, 264(25)14874–14879 (1989).

Farrow et al., "Synthesis of a gene for the protein kinase domain of the epidermal growth factor receptor and its expression in *Escherichia coli*," *Eur. J. Biochem.*, 184:361–365 (1989).

Ferretti, et al., "Total synthesis of a gene for bovine rhodopsin," *Proc. Natl. Acad. Sci. USA*, 83:599–603 (1986).

Foquet and Lubbert "Precise and efficient construction of synthetic genes," *Biotechniques*, 13(5):674–675 (1992).

Gearing et al., "Chemical synthesis of a mitochondrial gene designed for expression in the yeat nucleus," *Biochem. Int.*, 10(6):907–915 (1985).

Gurevich et al., "Chemical–enzymatic synthesis of the translation–enhancer gene 10 of phage T7 and function of olements of its structure," *Bioorg. Chem.*, 17(5):371–376 (1991).

Gurevich et al, "Construction of artificial genes by PCR methods using the synthetic template," *Bioorg. Khim.*, 23(6):492–496 (1997).

Harada et al., "Total synthesis of a gene for octopus rhodopsin and its preliminary expression," *J. Biochem.*, 110:501–507 (1991).

Henze et al., "Expression of the chemically synthesized coding region for the cytotoxin alpha–sarcin in *Escherichia coli* using a secretion cloning vector," *Eur J. Biochem.*, 192(1):127–131 (1990).

Hostomský et al., "Solid –phase assembly of cow colostrum trypsin inhibitor gene," *Nucleic Acid Research*, 15(12):4849–4855 (1987).

Ikehara et al., "Synthesis of a gene for human growth hormone and its expression in *Escherichia coli*," *Proc Natl. Acad, Sci. USA*, 81 (19):5956–5960 (1984).

Inaoka et al., "Chemical synthesis of the T4 endonucleases V gene and its expressin in *Escherichia coli*." *Nucleic Acids Symp. Ser.*, 17:105–108 (1986).

Kaji et al., "Studies on chemical synthesis of human cystatin a gene and its expressin in *Escherichia coli*," *J. Biochem (Tokyo)*, 105(1):143–147 (1989).

Kálmán et al., "Synthesis of a gene for human serum albumin and its expression in *saccharomyces cerevisiae*," *Nucleic Acids Res.*, 18(20):6075–6081 (1990).

Kaltenboek and Kousoulas "Efficient PCR production of a single–stranded DNA sequencing templates," *Methods Mol. Biol.*, 65:149–153 (1996).

Kash'yap et al., "Chemical–enzymatic synthesis and cloning in *Escherichia coli* of the gene coding human granulocyte-colony–stimulating factor," *Bioorg. Chem.*, 18(1):18–22 (1992).

Katunuma et al., "Total synthesis of the cystatin alpha gene and its expression in *E. coli*," *FEBS Lett.*, 238(1):116–118 (1988).

Kim et al., "Chemical synthesis and cloning of human beta–endorphin gene in *Escherichia coli*," *Appl. Biochem Biothechnol.*, 50(1):35–43 (1995).

Lashkari et al., "An automated multiplex oligonucleotide synthesizer: development of high throughput, low–cost DNA synthesis" *Proc. Natl. Acad. Sci. USA*, 92(17):7912–7915 (1995).

Lebedenko et al., "Synthesis and modification of genes through artificial splicing by directed ligation (ASDL)," *Nucleic Acids Symp. Ser.*, 24:215–216 (1991).

Lebedenko et al., "Method of artificial DNA splicing by directed ligation (SDL)," *Nucleic Acids, Res.*, 19(24):6757–6761 (1991).

Modesti, et al., "Chemical synthesis and expression of a gene coding for human muscle acylphophatase," *Biochim. Biophys. Acta.*, 1216(3):369–374 (1993).

Nagase et al. "Chemical synthesis of a human fibroblast interferon gene and its expression in *Escherichia coli*," *Nucleic Acids Symp. Ser.*, 12:83–86 (1983).

Prodromou and Pearl, "Recursive PCR: a novel technique for total gene synthesis," Protein Eng., 5(8):827–829 (1992).

Rayner et al., "MerMade: an oligodeoxyribonucleotide synthesizer for high throughput oligonucleotide production in dual 96–well plates" *Genome Research*, 8(7):741–747 (1998).

Roberts et al., "Chemical synthesis and expression of a calmodulin gene designed for site–specific mutagenesis," *Biochemistry*, 24(19):5090–5098 (1985).

Rosenthal et al. "Chemical–enzymatic synthesis, cloning and expression of a synthetic gene coding for an env protein fragment of the human T–cell leukemia virus type 1," *Nucleic Acids Symp. Ser.*, 18:233–236 (1987).

Sandhu et al., "Dual asymmetric PCR: one–step construction of synthetic genes," *Biotechniques*, 12(1):14–16 (1992).

Sindelar and Jaklevic, "High–throughput DNA synthesis in a multichannel format" *Nucleic Acid Res.*, 23(6):982–987 (1995).

Stemmer et al., "Single–step assembly of a gene and entire plasmid from large numbers of oligodeoxyribonucleotides" *Gene*, 164:49–53 (19995).

Strauss et al., "Chemical synthesis of a gene for human stefin A and its expression in *E. coli*," *Biol. Chem. Hoppe Seyler*, 369(9):1019–1030 (1988).

Strauss et al., "Chemical synthesis of a gene for human cystatin C and its expression in *E. coli*," *Biol. Chem. Hoppe Seyler*, 369:209–218 (1988).

Sulo and Martin, "Isolation and characterization of LIP5," *J. Biol. Chem.*, 268 (23):17634–17639 (1993).

Suwen et al., "Chemical synthesis and cloning of secretin gene," *Sci. Sin.* [B], 31 (6):687–694 (1988).

Tanaka et al., "Expression in *Escherichia coli* of chemically synthesized gene for a human immune interferon," *Nucleic Acids Symp. Ser.*, 11:29–32 (1982).

Thompson and Weber, "Construction and expression of a synthetic streptavidin–encoding gene in *Escherichia coli*," *Gene*, 136 (1–2):243–246 (1993).

Traub et al., "Gene sysnthesis, expression i *E. coli*, and in vivo refolding of pseudomonas and chromobacterium viscosum lipase and their chaparones" *Appl. Microbiol. Biotechnol.*, 55(2):198–204 (2001).

Wosnick et al., "Total chemical synthesis and expression in *Escherichia coli* of a maize glutathione–transferase (GTS) gene," *Gene*, 76:153–160 (1989).

Biomek Set-up

Genewriter - Oligonucleotide Pooling Plan

Perspective view of Genewriter Instrument

Assembly of Self assembling oligonucleotide arrays
Option 1

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1
gatcgttatt cgctcgatgc ttcga                                    25

<210> SEQ ID NO 2
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 2
gagctacgaa gctgactaaa gcgca                                    25

<210> SEQ ID NO 3
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 3
ctgatttcgc gtatactaat cctgt                                    25

<210> SEQ ID NO 4
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 4
gatcgttatt cgctcgatgc ttcgactgat ttcgcgtata ctaatcctgt          50

<210> SEQ ID NO 5
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 5
ggattccatt cgtcgattcg gccct                                    25

<210> SEQ ID NO 6
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 6
gttcaaatag aatgccctag ggatg                                    25

<210> SEQ ID NO 7
<211> LENGTH: 25

```
<212> TYPE: DNA
<213> ORGANISM: Artificial Sequence
<220> FEATURE:
<223> OTHER INFORMATION: synthetic oligonucleotide

<400> SEQUENCE: 7
cagctaagcc gggacaagtt tatct                                              25

<210> SEQ ID NO 8
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 8
ggattccatt cgtcgattcg gccggttcaa atagaatgcc ctagggatg                    49

<210> SEQ ID NO 9
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 9
gatgttctta taaccggaat ttccg                                              25

<210> SEQ ID NO 10
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 10
gatcttgtta taagccgaat ttcgggatt ccattcgtcg attcggccct                    50

<210> SEQ ID NO 11
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 11
ttcaacttaa agggcctaag gtaaga                                             26
```

METHOD FOR ASSEMBLY OF A POLYNUCLEOTIDE ENCODING A TARGET POLYPEPTIDE

This application is a continuation-in-part of application Ser. No. 09/554,929, filed in the United States on May 12, 2000, as a national stage application of International Application No. PCT/US98/19312, filed Sep. 16, 1998, which claims the benefit of priority of provisional application Serial No. 60/059,017, filed Sep. 16, 1997, now abandoned, the contents of each of which are hereby incorporated by reference into the present disclosure.

BACKGROUND OF THE INVENTION

The present invention relates generally to the area of bioinformatics and more specifically to methods, algorithms and apparatus for computer directed polynucleotide assembly. The invention further relates to the production of polypeptides encoded by polynucleotides assembled by the invention.

Enzymes, antibodies, receptors and ligands are polypeptides that have evolved by selective pressure to perform very specific biological functions within the milieu of a living organism. The use of a polypeptide for specific technological applications may require the polypeptide to function in environments or on substrates for which it was not evolutionarily selected. Polypeptides isolated from microorganisms that thrive in extreme environments provide ample evidence that these molecules are, in general, malleable with regard to structure and function. However, the process for isolating a polypeptide from its native environment is expensive and time consuming. Thus, new methods for synthetically evolving genetic material encoding a polypeptide possessing a desired activity are needed.

There are two ways to obtain genetic material for genetic engineering manipulations: (1) isolation and purification of a polynucleotide in the form of DNA or RNA from natural sources or (2) the synthesis of a polynucleotide using various chemical-enzymatic approaches. The former approach is limited to naturally-occurring sequences that do not easily lend themselves to specific modification. The latter approach is much more complicated and labor-intensive. However, the chemical-enzymatic approach has many attractive features including the possibility of preparing, without any significant limitations, any desirable polynucleotide sequence.

Two general methods currently exist for the synthetic assembly of oligonucleotides into long polynucleotide fragments. First, oligonucleotides covering the entire sequence to be synthesized are first allowed to anneal, and then the nicks are repaired with ligase. The fragment is then cloned directly, or cloned after amplification by the polymerase chain reaction (PCR). The polynucleotide is subsequently used for in vitro assembly into longer sequences. The second general method for gene synthesis utilizes polymerase to fill in single-stranded gaps in the annealed pairs of oligonucleotides. After the polymerase reaction, single-stranded regions of oligonucleotides become double-stranded, and after digestion with restriction endonuclease, can be cloned directly or used for further assembly of longer sequences by ligating different double-stranded fragments. Typically, subsequent to the polymerase reaction, each segment must be cloned which significantly delays the synthesis of long DNA fragments and greatly decreases the efficiency of this approach.

The creation of entirely novel polynucleotides, or the substantial modification of existing polynucleotides, is extremely time consuming, expensive, requires complex and multiple steps, and in some cases is impossible. Therefore, there exists a great need for an efficient means to assemble synthetic polynucleotides of any desired sequence. Such a method could be universally applied. For example, the method could be used to efficiently make an array of polynucleotides having specific substitutions in a known sequence that is expressed and screened for improved function. The present invention satisfies these needs by providing efficient and powerful methods and compositions for the synthesis of a target polynucleotide encoding a target polypeptide.

SUMMARY OF THE INVENTION

The present invention provides methods for the synthetic assembly of polynucleotides and related algorithms. In particular, the present invention provides fast and efficient methods for generating any nucleic acid sequence, including entire genes, chromosomal segments, chromosomes and genomes. Because this approach is based on a completely synthetic approach, there are no limitations, such as the availability of existing nucleic acids, to hinder the construction of even very large segments of nucleic acid.

BRIEF DESCRIPTION OF THE DRAWINGS

Like reference symbols in the various drawings indicate like elements.

FIG. 2 depicts the oligonucleotide pooling plan where F oligonucleotides and R oligonucleotides are annealed to form a contiguous polynucleotide.

DETAILED DESCRIPTION OF THE INVENTION

Figure 1:
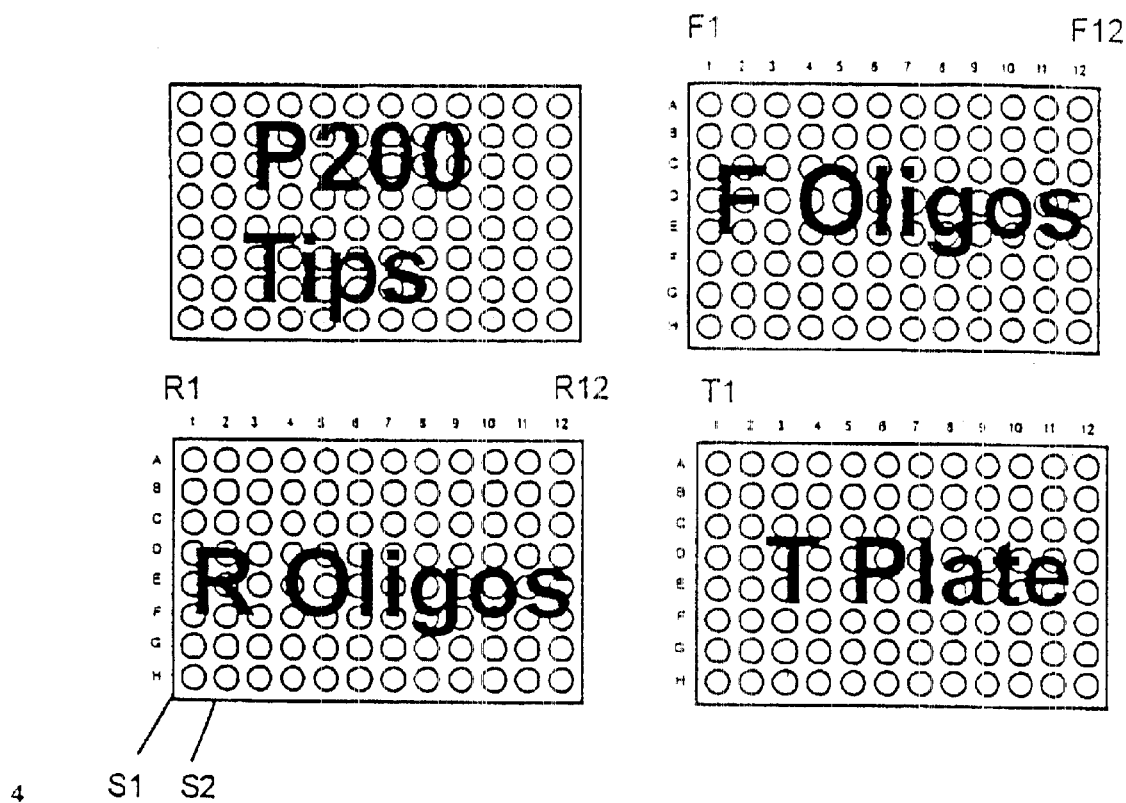
FIG. 1 depicts 96 well plates for of F (i.e., "forward" or "plus strand") oligonucleotide synthesis, R (i.e., "reverse" or "minus strand") oligonucleotide synthesis, and a T (i.e., "temperature") plate for the annealing of F and T oligonucleotides.

The elucidation of the complete sequence of complex genomes, including the human genome, allows for large scale functional approaches to genetics. The present invention provides a novel approach to utilizing the results of genomic sequence information by computer-directed polynucleotide assembly based upon information available in databases such as the human genome database. Specifically, the present invention can be used to synthesize, assemble and select a novel, synthetic target polynucleotide sequence encoding a target polypeptide. The target polynucleotide can encode a target polypeptide that exhibits enhanced or altered biological activity as compared to a model polypeptide encoded by a natural (wild-type) or model polynucleotide sequence. Subsequently, standard assays can be used to survey the activity of an expressed target polypeptide. For example, the expressed target polypeptide can be assayed to determine its ability to carry out the function of the corresponding model polypeptide or to determine whether a target polypeptide exhibiting a new function has been produced. Thus, the present invention provides a means to direct the synthetic evolution of a model polypeptide by computer-directed synthesis of a polynucleotide encoding a target polypeptide derived from a model polypeptide.

In one embodiment, the invention provides a method of synthesizing a target polynucleotide by providing a target polynucleotide sequence and identifying at least one initiating oligonucleotide present in the target polynucleotide which includes at least one plus strand oligonucleotide annealed to at least one minus strand oligonucleotide resulting in a partially double-stranded polynucleotide comprised of a 5' overhang and a 3' overhang. Subsequently, a next most terminal oligonucleotide can be added in a process that is repeated systematically to sequentially assemble a double-stranded polynucleotide. In the various embodiments provided by the assembly methods of the invention, a next most terminal oligonucleotide, which can be either single-stranded or double-stranded, can be added so as to extend the initiating oligonucleotide in an alternating bidirectional manner, in a uni-directional manner, or any combination thereof.

As used herein, a "target polynucleotide sequence" includes any nucleic acid sequence suitable for encoding a target polypeptide that can be synthesized by a method of the invention. A target polynucleotide sequence can be used to generate a target polynucleotide using an apparatus capable of assembling nucleic sequences. Generally, a target polynucleotide sequence is a linear segment of DNA having a double-stranded region; the segment can be of any length sufficiently long to be created by the hybridization of at least two oligonucleotides have complementary regions. It is contemplated that a target polynucleotide can be 100, 200, 300, 400, 800, 1000, 1500, 2000, 4000, 8000, 10000, 12000, 18,000, 20,000, 40,000, 80,000 or more base pairs in length. The methods of the present invention can be utilized to create entire artificial genomes of lengths comparable to known bacterial, yeast, viral, mammalian, amphibian, reptilian, or avian genomes. In more particular embodiments, the target polynucleotide is a gene encoding a polypeptide of interest. The target polynucleotide can further include non-coding elements such as origins of replication, telomeres, promoters, enhancers, transcription and translation start and stop signals, introns, exon splice sites, chromatin scaffold components and other regulatory sequences. The target polynucleotide can comprise multiple genes, chromosomal segments, chromosomes and even entire genomes. A polynucleotide of the invention can be derived from prokaryotic or eukaryotic sequences including bacterial, yeast, viral, mammalian, amphibian, reptilian, avian, plants, archebacteria and other DNA containing living organisms.

An "oligonucleotide", as used herein, is defined as a molecule comprised of two or more deoxyribonucleotides or ribonucleotides, preferably more than three. Oligonucleotides are small DNA segments, single-stranded or double-stranded, comprised of the nucleotide bases linked through phosphate bonds. The exact size of an oligonucleotide depends on many factors, such as the reaction temperature, salt concentration, the presence of denaturants such as formamide, and the degree of complementarity with the sequence to which the oligonucleotide is intended to hybridize.

Nucleotides are present in either DNA or RNA and encompass adenine, cytosine, guanine and thymine or uracil, respectively, as base, and a sugar moiety being deoxyribose or ribose, respectively. It will be appreciated however that other modified bases capable of base pairing with one of the conventional bases, adenine, cytosine, guanine, thymine and uracil, can be used in an oligonucleotide employed in the present invention. Such modified bases include for example 8-azaguanine and hypoxanthine. If desired the nucleotides can carry a label or marker so that on incorporation into a primer extension product, they augment the signal associated with the primer extension product, for example for capture on to solid phase.

A plus strand oligonucleotide, by convention, includes a short, single-stranded DNA segment that starts with the 5' end to the left as one reads the sequence. A minus strand oligonucleotide includes a short, single-stranded DNA segment that starts with the 3' end to the left as one reads the sequence. Methods of synthesizing oligonucleotides are found in, for example, Oligonucleotide Synthesis: *A Practical Approach*, Gate, ed., IRL Press, Oxford (1984), incorporated herein by reference in its entirety. Solid-phase synthesis techniques have been provided for the synthesis of several peptide sequences on, for example, a number of "pins" (See e.g., Geysen et al., *J. Immun. Meth.* (1987) 102:259–274, incorporated herein by reference in its entirety).

Additional methods of forming large arrays of oligonucleotides and other polymer sequences in a short period of time have been devised. Of particular note, Pirrung et al., U.S. Pat. No. 5,143,854 (see also PCT Application No. WO 90/15070), Fodor et al., PCT Publication No. WO 92/10092 and Winkler et al., U.S. Pat. No. 6,136,269, all incorporated herein by reference, disclose methods of forming vast arrays of polymer sequences using, for example, light-directed synthesis techniques. See also, Fodor et al., *Science* (1991) 251:767–777, also incorporated herein by reference in its entirety. Some work has been done to automate synthesis of polymer arrays. For example, Southern, PCT Application No. WO 89/10977, describes the use of a conventional pen plotter to deposit three different monomers at twelve distinct locations on a substrate.

An "initiating" oligonucleotide or polynucleotide sequence, as used herein, is an oligonucleotide or polynucleotide sequence that serves as the first or starting sequence that is sequentially extended by systematic addition of a next most terminal oligonucleotides or a next most terminal component polynucleotide. An intiating oligonucleotide or polynucleotide sequence can have a 5' overhang, a 3' overhang, or a 5' and a 3' overhang of either strand. An intiating oligonucleotide or polynucleotide sequence can be extended in an alternating bi-directional manner, in a uni-directional manner or any combination thereof. An initiating oligonucleotide or polynucleotide sequence can be contained in a target polynucleotide sequence and identified by an algorithm of the invention. In this regard, an initiating oligonucleotide or polynucleotide sequence contained in a target polynucleotide sequence can be either the 5' most terminal oligonucleotide, the 3' most terminal oligonucleotide, or neither the 3' nor the 5' most terminal nucleotide of the target polynucleotide sequence, depending on whether the target polynucleotide is assembled starting from the middle versus starting from one of the two ends. If an initiating oligonucleotide or polynucleotide sequence contained in a target polynucleotide sequence represents either the 5' most terminal oligonucleotide, the 3' most terminal oligonucleotide of the target polynucleotide, it can encompass one overhang.

For ligation assembly of a target polynucleotide, an initiating oligonucleotide begins assembly by providing an anchor for hybridization of subsequent oligonucleotides contiguous with the initiating oligonucleotide. Thus, for ligation assembly, an initiating oligonucleotide is partially double-stranded nucleic acid thereby providing single-stranded overhang(s) for annealing of a contiguous, double-stranded nucleic acid molecule. For primer extension assembly of a target polynucleotide, an initiating oligonucleotide begins assembly by providing a template for hybridization of subsequent oligonucleotides contiguous with the initiating oligonucleotide. Thus, for primer extension assembly, an initiating oligonucleotide can be partially double-stranded or fully double-stranded.

As used herein, the term "next most terminal" oligonucleotide refers to an oligonucleotide that is added to an extended intiating oligonucleotide at either the 5' or the 3' end. A next most terminal oligonucleotide can be either single-stranded, partially double-stranded or fully double-stranded. In the sequential methods of the invention utilizing cycles of sequentially adding the next most terminal oligonucleotide to the extending double-stranded oligonucleotide, the next most terminal oligonucleotide has at least one overhang that is complementary to a 3' or 5' overhang sequence belonging to either the plus or minus strand of the extending double-stranded oligonucleotide.

As used herein, the terms "5' most terminal" and "3' most terminal" refer to a single-stranded or double-stranded oligonucleotide or polynucleotide that encompasses either the physical beginning or the end of a target polynucleotide sequence. As described above, an initiating oligonucleotide or polynucleotide used in the sequential assembly methods of the invention can, for example, be a 5' most terminal or a 3' most terminal oligonucleotide.

As used herein, the term "enzymatic synthesis" refers to assembly of polynucleotides that utilizes one or more enzymes for functions including, for example, polymerization, primer extension, ligation or mismatch repair. As described herein, the polynucleotide assembly methods of the invention can be performed both by both enzymatic synthesis and non-enzymatic synthesis. Enzymatic primer extension refers to polynucleotide synthesis methods that include primer extension via an enzymatic reaction including, for example, polymerase chain reaction (PCR) and ligase chain reaction (LCR), which utilize thermostable polymerase and thermostable ligase, respectively, to synthesize polynucleotides. Furthermore, as used herein "enzymatic polymerization" refers to assembly of a polynucleotide or oligonucleotide that utitilizes a natural or recombinant polymerase for extension including, for example, polymerase chain reaction (PCR).

The present invention provides fast and efficient methods for assembly of a polynucleotide, including entire genes, chromosomal segments or fragments, chromosomes and genomes. Because the invention methods are based on a completely synthetic approach, there are no limitations, such as the availability of existing nucleic acids or the complexities of site-specific mutagenesis, to hinder the construction of even very large segments of nucleic acid. In particular, art-known methods for the synthetic assembly of oligonucleotides into long DNA fragments generally utilize polymerase to fill in single-stranded gaps in annealed pairs of oligonucleotides. However, after the polymerase reaction, each segment must be cloned, a step which significantly delays the synthesis of long polynucleotide fragments and greatly decreases the efficiency of the approach. Additionally, the approach can be used only for small DNA fragments.

Other art-known methods of polynucleotide synthesis include PCR based techniques that involve assembly of overlapping oligonucleotides performed by a thermostable DNA polymerase during repeated cycles by melting, annealing and polymerization. A key disadvantage of PCR mediated methods is that complex mispriming events negatively affect the correctness of a resulting assembled polynucleotide. In addition, the low fidelity of thermostable DNA polymerase influences the reliability of this technology with increased number of PCR steps. Other known methods for polynucleotide synthesis involve the ligation of two or more polynucleotide strands without use of a template and have the disadvantage of only being able to synthesize short genes of about 200 base pairs.

In one embodiment, the invention provides a method of assembling a double-stranded polynucleotide comprising a) selecting a partially double-stranded initiating oligonucleotide, wherein the initiating oligonucleotide comprises at least one overhang; b) contacting the partially double-stranded initiating oligonucleotide with a next most terminal oligonucleotide, wherein the next most terminal oligonucleotide is contiguous with the initiating oligonucleotide and comprises at least one overhang, and wherein the at least one overhang of the next most terminal oligonucleotide is complementary to at least one overhang of the initiating oligonucleotide; and c) repeating (b) to sequentially add the next most terminal oligonucleotide to the extended initiating oligonucleotide, whereby the double-stranded polynucleotide is synthesized.

In another embodiment, the invention provides a method of synthesizing a target polynucleotide sequence comprising: a) providing a target polynucleotide sequence; b) identifying at least one initiating polynucleotide present in the target polynucleotide which includes at least one plus strand oligonucleotide annealed to at least one minus strand oligonucleotide resulting in a partially double-stranded polynucleotide comprised of a 5' overhang and a 3' overhang; c) identifying a second polynucleotide present in the target polynucleotide which is contiguous with the initiating polynucleotide and includes at least one plus strand oligonucleotide annealed to at least one minus strand oligonucleotide resulting in a partially double-stranded polynucleotide comprised of a 5' overhang, a 3' overhang, or a 5' overhang and a 3' overhang, where at least one overhang of the second polynucleotide is complementary to at least one overhang of the initiating polynucleotide; d) identifying a third polynucleotide present in the target polynucleotide which is contiguous with the initiating sequence and includes at least one plus strand oligonucleotide annealed to at least one minus strand oligonucleotide resulting in a partially double-stranded polynucleotide comprised of a 5' overhang, a 3' overhang, or a 5' overhang and a 3' overhang, where at least one overhang of the third polynucleotide is complementary to at least one overhang of the initiating polynucleotide which is not complementary to an overhang of the second polynucleotide; e) contacting the initiating polynucleotide with the second polynucleotide and the third polynucleotide under conditions and for such time suitable for annealing, the contacting resulting in a contiguous double-stranded polynucleotide, resulting in the bi-directional extension of the initiating polynucleotide; f) in the absence of primer extension, optionally contacting the mixture of e) with a ligase under conditions suitable for ligation; and g) optionally repeating (b) through (f) to sequentially add double-stranded polynucleotides to the extended initiating polynucleotide through repeated cycles of annealing and ligation, whereby a target polynucleotide is synthesized.

The invention further provides a method of assembling a target polynucleotide comprising: a) providing a target polynucleotide sequence; b) identifying at least one partially double-stranded initiating oligonucleotide present in the target polynucleotide, wherein the initiating oligonucleotide comprises a 5' overhang and a 3' overhang; c) identifying a next most terminal oligonucleotide present in the target polynucleotide, wherein the next most terminal oligonucleotide is contiguous with the initiating oligonucleotide and comprises a 5' overhang and a 3' overhang, wherein at least one overhang of the next most terminal oligonucleotide is complementary to at least one overhang of the initiating oligonucleotide; d) contacting the initiating oligonucleotide with the next most terminal oligonucleotide under such conditions and for such time suitable for annealing, wherein the initiating sequence is extended; and e) optionally repeating (a) through (d) to sequentially add the next most terminal oligonucleotide to the extended initiating oligonucleotide, whereby a target polynucleotide is synthesized.

The invention also provides a method of assembling a polynucleotide comprising: a) providing a partially double-stranded initiating oligonucleotide present, wherein the initiating oligonucleotide comprises a 5' overhang and a 3' overhang; c) identifying a next most terminal oligonucleotide, wherein the next most terminal oligonucleotide is contiguous with the initiating oligonucleotide and comprises a 5' overhang and a 3' overhang, wherein at least one overhang of the next most terminal oligonucleotide is complementary to at least one overhang of the initiating oligonucleotide; d) contacting the initiating oligonucleotide with the next most terminal oligonucleotide under such conditions and for such time suitable for annealing, wherein the initiating sequence is extended; and e) optionally repeating (a) through (d) to sequentially add the next most terminal oligonucleotides to the extended initiating oligonucleotide, whereby a polynucleotide is synthesized.

The invention further provides a method of synthesizing a target polynucleotide comprising: a) providing a target polynucleotide sequence derived from a model sequence; b) identifying at least one initiating polynucleotide sequence present in the target polynucleotide sequence of a), wherein the initiating polynucleotide contains: 1) a first plus strand oligonucleotide; 2) a second plus strand oligonucleotide contiguous with the first plus strand oligonucleotide; and 3) a minus strand oligonucleotide including a first contiguous sequence which is at least partially complementary to the first plus strand oligonucleotide and second contiguous sequence which is at least partially complementary to the second plus strand oligonucleotide; c) annealing the first plus strand oligonucleotide and the second plus strand oligonucleotide to the minus strand oligonucleotide of b) resulting in a partially double-stranded initiating polynucleotide including a 5' overhang and a 3' overhang; d) identifying a second polynucleotide sequence present in the target polynucleotide sequence of a), wherein the second polynucleotide sequence is contiguous with the initiating polynucleotide sequence and contains: 1) a first plus strand oligonucleotide; 2) a second plus strand oligonucleotide contiguous with the first plus strand oligonucleotide; and 3) a minus strand oligonucleotide comprising a first contiguous sequence which is at least partially complementary to the first plus strand oligonucleotide and second contiguous sequence which is at least partially complementary to the second plus strand oligonucleotide; e) annealing the first plus strand oligonucleotide and the second plus strand oligonucleotide to the minus strand oligonucleotide of d) resulting in a partially double-stranded second polynucleotide, wherein at least one overhang of the second polynucleotide is complementary to at least one overhang of the initiating polynucleotide; f) identifying a third polynucleotide present in the target polynucleotide of a), wherein the third polynucleotide is contiguous with the initiating sequence and contains: 1) a first plus strand oligonucleotide;

2) a second plus strand oligonucleotide contiguous with the first plus strand oligonucleotide; and 3) a minus strand oligonucleotide comprising a first contiguous sequence which is at least partially complementary to the first plus strand oligonucleotide and second contiguous sequence which is at least partially complementary to the second plus strand oligonucleotide; g) annealing the first plus strand oligonucleotide and the second plus strand oligonucleotide to the minus strand oligonucleotide of f) resulting in a partially double-stranded second polynucleotide, wherein at least one overhang of the third polynucleotide is complementary to at least one overhang of the initiating polynucleotide and not complementary to an overhang of the second polynucleotide; h) contacting the initiating polynucleotide of c) with the second polynucleotide of e) and the third polynucleotide of g) under conditions and for such time suitable for annealing, the contacting resulting in a contiguous double-stranded polynucleotide, wherein the initiating sequence is extended bi-directionally; i) in the absence of primer extension, optionally contacting the mixture of h) with a ligase under conditions suitable for ligation; and j) optionally repeating b) through i) to sequentially add double-stranded polynucleotides to the extended initiating polynucleotide through repeated cycles of annealing and ligation, whereby a target polynucleotide is synthesized.

The invention further provides a method of synthesizing a target polynucleotide comprising: a) providing a target polynucleotide sequence derived from a model sequence; b) identifying at least one initiating polynucleotide sequence present in the target polynucleotide sequence of a), wherein the initiating polynucleotide includes 1) a first plus strand oligonucleotide; 2) a second plus strand oligonucleotide contiguous with the first plus strand oligonucleotide; and 3) a minus strand oligonucleotide including a first contiguous sequence which is at least partially complementary to the first plus strand oligonucleotide and second contiguous sequence which is at least partially complementary to the second plus strand oligonucleotide; c) annealing the first plus strand oligonucleotide and the second plus strand oligonucleotide to the minus strand oligonucleotide of b) resulting in a partially double-stranded initiating polynucleotide including a 5' overhang and a 3' overhang; d) identifying a second polynucleotide sequence present in the target polynucleotide sequence of a), wherein the second polynucleotide sequence is contiguous with the initiating polynucleotide sequence and contains: 1) a first plus strand oligonucleotide; 2) a second plus strand oligonucleotide contiguous with the first plus strand oligonucleotide; and 3) a minus strand oligonucleotide comprising a first contiguous sequence which is at least partially complementary to the first plus strand oligonucleotide and second contiguous sequence which is at least partially complementary to the second plus strand oligonucleotide; e) annealing the first plus strand oligonucleotide and the second plus strand oligonucleotide to the minus strand oligonucleotide of d) resulting in a partially double-stranded second polynucleotide, wherein at least one overhang of the second polynucleotide is complementary to at least one overhang of the initiating polynucleotide; h) contacting the initiating polynucleotide of c) with the second polynucleotide of e) under conditions and for such time suitable for annealing, the contacting resulting in a contiguous double-stranded polynucleotide, wherein the initiating sequence is extended; i) in the absence of primer extension, optionally contacting the mixture of h) with a ligase under conditions suitable for ligation; and j) optionally repeating b) through i) to sequentially add double-stranded polynucleotides to the extended initiating polynucleotide through repeated cycles of annealing and ligation, whereby a target polynucleotide is synthesized.

The invention further provides a method of synthesizing a target polynucleotide comprising a) providing a first polynucleotide including 1) a first plus strand oligonucleotide; 2) a second plus strand oligonucleotide contiguous with the first plus strand oligonucleotide; and 3) a minus strand oligonucleotide including a first contiguous sequence which is at least partially complementary to the first plus strand oligonucleotide and second contiguous sequence which is at least partially complementary to the second plus strand oligonucleotide; b) annealing the first plus strand oligonucleotide and the second plus strand oligonucleotide to the minus strand oligonucleotide of a) resulting in a partially double-stranded initiating polynucleotide including a 5' overhang and a 3' overhang; c) identifying a second polynucleotide sequence present in the target polynucleotide sequence of a), wherein the second polynucleotide sequence is contiguous with the initiating polynucleotide sequence and includes: 1) a first plus strand oligonucleotide; 2) a second plus strand oligonucleotide contiguous with the first plus strand oligonucleotide; and 3) a minus strand oligonucleotide comprising a first contiguous sequence which is at least partially complementary to the first plus strand oligonucleotide and second contiguous sequence which is at least partially complementary to the second plus strand oligonucleotide; e) annealing the first plus strand oligonucleotide and the second plus strand oligonucleotide to the minus strand oligonucleotide of d) resulting in a partially double-stranded second polynucleotide, wherein at least one overhang of the second polynucleotide is complementary to at least one overhang of the initiating polynucleotide; h) contacting the initiating polynucleotide of c) with the second polynucleotide of e) under conditions and for such time suitable for annealing, the contacting resulting in a contiguous double-stranded polynucleotide, wherein the initiating sequence is extended; i) in the absence of primer extension, optionally contacting the mixture of h) with a ligase under conditions suitable for ligation; and j) optionally repeating b) through i) to sequentially add double-stranded polynucleotides to the extended initiating polynucleotide through repeated cycles of annealing and ligation, whereby a target polynucleotide is synthesized.

The invention further provides a method of synthesizing a target polynucleotide comprising: a) providing a first plus strand oligonucleotide; b) a first minus strand oligonucleotide which is at least partially complementary to the first plus strand oligonucleotide; c) annealing the first plus strand oligonucleotide to the first minus strand oligonucleotide resulting in a partially double-stranded initiating polynucleotide including at least one overhang; d) adding a next most terminal single-stranded oligonucleotide that is at least partially complementary to the overhang of the double-stranded initiating polynucleotide; e) annealing the next most terminal single-stranded oligonucleotide to the double-stranded initiating polynucleotide; d) resulting in a partially double-stranded second polynucleotide, including at least one overhang; h) in the absence of primer extension, optionally contacting the mixture of h) with a ligase under conditions suitable for ligation; and j) optionally repeating b) through i) to sequentially add single-stranded polynucleotides to the extended initiating polynucleotide through repeated cycles of annealing and ligation, whereby a target polynucleotide is synthesized.

In another embodiment, the invention provides a method for synthesizing a target polynucleotide, comprising: a)

providing a target polynucleotide sequence derived from a model sequence; b) identifying at least one initiating polynucleotide present in the target polynucleotide which includes at least one plus strand oligonucleotide annealed to at least one minus strand oligonucleotide; c) contacting the initiating polynucleotide under conditions suitable for primer annealing with a first oligonucleotide having partial complementarity to the 3' portion of the plus strand of the initiating polynucleotide, and a second oligonucleotide having partial complementarity to the 3' portion of the minus strand of the initiating polynucleotide; d) catalyzing under conditions suitable for primer extension: 1) polynucleotide synthesis from the 3'-hydroxyl of the plus strand of the initiating polynucleotide; 2) polynucleotide synthesis from the 3'-hydroxyl of the annealed first oligonucleotide; 3) polynucleotide synthesis from the 3'-hydroxyl of the minus strand of the initiating polynucleotide; and 4) polynucleotide synthesis from the 3'-hydroxyl of the annealed second oligonucleotide, resulting in the bi-directional extension of the initiating sequence thereby forming a nascent extended initiating polynucleotide; e) contacting the extended initiating polynucleotide of d) under conditions suitable for primer annealing with a third oligonucleotide having partial complementarity to the 3' portion of the plus strand of the extended initiating polynucleotide, and a fourth oligonucleotide having partial complementarity to the 3' portion of the minus strand of the extended initiating polynucleotide; f) catalyzing under conditions suitable for primer extension: 1) polynucleotide synthesis from the 3'-hydroxyl of the plus strand of the extended initiating polynucleotide; 2) polynucleotide synthesis from the 3'-hydroxyl of the annealed third oligonucleotide; 3) polynucleotide synthesis from the 3'-hydroxyl of the minus strand of the extended initiating polynucleotide; and 4) polynucleotide synthesis from the 3'-hydroxyl of the annealed fourth oligonucleotide, resulting in the bi-directional extension of the initiating sequence thereby forming a nascent extended initiating polynucleotide; and g) optionally repeating e) through f) as desired, resulting in formation of the target polynucleotide sequence.

The invention further provides a method for isolating a target polypeptide encoded by a target polynucleotide generated by a method of the invention comprising: a) incorporating the target polynucleotide in an expression vector; b) introducing the expression vector into a suitable host cell; c) culturing the cell under conditions and for such time as to promote the expression of the target polypeptide encoded by the target polynucleotide; and d) isolating the target polypeptide.

The invention further provides a method of synthesizing a target polynucleotide comprising: a) providing a target polynucleotide sequence derived from a model sequence; b) chemically synthesizing a plurality of single-stranded oligonucleotides each of which is partially complementary to at least one oligonucleotide present in the plurality, where the sequence of the plurality of oligonucleotides is a contiguous sequence of the target polynucleotide; c) contacting the partially complementary oligonucleotides under conditions and for such time suitable for annealing, the contacting resulting in a plurality of partially double-stranded polynucleotides, where each double-stranded polynucleotide includes a 5' overhang and a 3' overhang; d) identifying at least one initiating polynucleotide derived from the model sequence present in the plurality of double-stranded polynucleotides; e) in the absence of primer extension, subjecting a mixture including the initiating polynucleotide and 1) a double-stranded polynucleotide that will anneal to the 5' portion of the initiating and sequence; 2) a double-stranded polynucleotide that will anneal to the 3' portion of the initiating polynucleotide; and 3) a DNA ligase under conditions suitable for annealing and ligation, wherein the initiating polynucleotide is extended bi-directionally; f) sequentially annealing double-stranded polynucleotides to the extended initiating polynucleotide through repeated cycles of annealing, whereby the target polynucleotide is produced.

In addition to the sequential assembly methods described above, the invention also provides set assembly methods, in which two sets of oligonucleotides are synthesized and subsequently annealed. In this regard, the invention also provides a method of assembling a double-stranded polynucleotide, comprising: (a) chemically synthesizing a first set of oligonucleotides of at least 25 bases comprising a first strand of a double-stranded polynucleotide; (b) chemically synthesizing a second set of oligonucleotides of at least 25 bases comprising a second complementary strand of the double-stranded polynucleotide, each of the oligonucleotides within the second set of the oligonucleotides overlapping with at least one oligonucleotide within the first set of the oligonucleotides, and (c) annealing the first and second sets of oligonucleotides to produce a double-stranded polynucleotide in the absence of enzymatic synthesis.

A double-stranded polynucleotide produced by the assembly methods of the invention can be, for example, about 100, 200, 300, 400, 500, 600, 700, 800, 900, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$ or more base pairs in length. As described above, in one embodiment of the invention, two sets of oligonucleotides can generated such that the entire plus and minus strands of the gene is represented. The oligonucleotide sets can be comprised of oligonucleotides of between about 15 and 150 bases, between about 20 and 100 bases, between about 25 and 75 bases, between about 30 and 50 bases. Specific lengths include, for example, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 150 or more bases.

Depending on the size, the overlap between the oligonucleotides of the two sets may be designed to be about 50 percent of the length of the oligonucleotide or between about 5 and 75 bases per oligonucleotide pair, for example, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 90, 100 or more bases. The sets can be designed such that complementary pairing with the first and second sets results in overlap of paired sequences, as each oligonucleotide of the first set is complementary with regions from two oligonucleotides of the second set, with the possible exception of the terminal oligonucleotides. The first and the second sets of oligonucleotides can optionally be annealed in a single mixture and treated with a ligating enzyme.

The invention further provides a method of assembling a double-stranded replication-competent polynucleotide, comprising: (a) chemically synthesizing a first set of oligonucleotides comprising a first strand of a double-stranded replication-competent polynucleotide having a coding region and a regulatory region; (b) chemically synthesizing a second set of oligonucleotides comprising a second complementary strand of the double-stranded replication-competent polynucleotide having a coding region and a regulatory region, each of the oligonucleotides within the second set of the oligonucleotides overlapping with at least one oligonucleotide within the first set of the oligonucleotides, and (c) annealing the first and second sets of oligonucleotides to produce a double-stranded replication-competent polynucleotide having a coding region and a regulatory region.

The set assembly methods of the invention can further be combined with the sequential assembly methods to assemble a double-stranded polynucleotide. As used heren, the term "component polynucleotide" when used in reference to a method of assembly that combines the set and sequential assembly methods provided by the invention, refers to a polynucleotide that is prepared by synthesizing and annealing of two separate sets of oligonucleotides. A component polynucleotide is subsequently incorporated into a larger polynucleotide via the sequential assembly methods provided by the invention.

Thus, the invention provides a method of assembling a double-stranded polynucleotide comprising: a) chemically synthesizing a first set of oligonucleotides comprising a first strand of a double-stranded polynucleotide; b) chemically synthesizing a second set of oligonucleotides comprising a second complementary strand of the double-stranded polynucleotide, each of the oligonucleotides within the second set of the oligonucleotides overlapping with at least one oligonucleotide within the first set of the oligonucleotides; and c) annealing the first and second sets of oligonucleotides to produce a partially double-stranded component polynucleotide; d) repeating steps (a) through (c) to prepare a series of partially double-stranded component polynucleotides; e) selecting at least one partially double-stranded component polynucleotide present in the target polynucleotide to serve as the initiating polynucleotide, wherein the initiating polynucleotide comprises a 5' overhang and a 3' overhang; f) adding the next most terminal component polynucleotide, wherein the next most terminal component polynucleotide comprises at least one overhang that is complementary to at least one overhang of the initiating polynucleotide; g) contacting the initiating polynucleotide with the next most terminal component polynucleotide under such conditions and for such time suitable for annealing, wherein the initiating sequence is extended; and h) optionally repeating (e) through (g) to sequentially add the next most terminal component polynucleotides to the extended initiating polynucleotide, whereby a target polynucleotide is assembled in the absence of enzymatic synthesis.

The assembly methods of the invention can encompass an initial step of providing or selecting a target polynucleotide to be assembled or can be performed without a predetermined target to assemble a polynucleotide of random sequence, for example, to generate a random library. Alternatively, the assembly methods of the invention can be utilized to assemble a polynucleotide that encompasses a target sequence, but also contains a random sequence, for example, to generate a biased library. The invention provides a computer program, stored on a computer-readable medium, for generating a target polynucleotide sequence derived from a model sequence, the computer program comprising instructions for causing a computer system to: a) identify an initiating polynucleotide sequence contained in the target polynucleotide sequence; b) parse the target polynucleotide sequence into multiply distinct, partially complementary, oligonucleotides; c) control assembly of the target polynucleotide sequence by controlling the bi-directional extension of the initiating polynucleotide sequence by the sequential addition of partially complementary oligonucleotides resulting in a contiguous double-stranded polynucleotide.

The invention further provides a method for automated synthesis of a target polynucleotide sequence, including: a) providing the user with an opportunity to communicate a desired target polynucleotide sequence; b) allowing the user to transmit the desired target polynucleotide sequence to a server; c) providing the user with a unique designation; d) obtaining the transmitted target polynucleotide sequence provided by the user.

The invention further provides a method for automated synthesis of a polynucleotide sequence, including: a) providing a user with a mechanism for communicating a model polynucleotide sequence; b) optionally providing the user with an opportunity to communicate at least one desired modification to the model sequence if desired; c) allowing the user to transmit the model sequence and desired modification to a server; d) providing user with a unique designation; e) obtaining the transmitted model sequence and optional desired modification provided by the user; f) inputting into a programmed computer, through an input device, data including at least a portion of the model polynucleotide sequence; g) determining, using the processor, the sequence of the model polynucleotide sequence containing the desired modification; h) further determining, using the processor, at least one initiating polynucleotide sequence present in the model polynucleotide sequence; i) selecting, using the processor, a model for synthesizing the modified model polynucleotide sequence based on the position of the initiating sequence in the model polynucleotide sequence; and j) outputting, to the output device, the results of the at least one determination.

Unless otherwise defined, all technical and scientific terms used herein have the same meaning as commonly understood by one of ordinary skill in the art to which this invention belongs. For example, the one letter and three letter abbreviations for amino acids and the one-letter abbreviations for nucleotides are commonly understood. Although methods and materials similar or equivalent to those described herein can be used in the practice or testing of the present invention, suitable methods and materials are described below. In addition, the materials, methods and examples are illustrative only and not intended to be limiting. All publications, patent applications, patents, and other references mentioned herein are incorporated by reference in their entirety. In case of conflict, the present specification, including definitions, will control.

The methods described above are collectively referred to as the polynucleotide assembly methods of the invention. The polynucleotide assembly methods of the invention can be performed in combination with or in the absence of enzymatic synthesis methods. Enzymatic synthesis methods include, for example, enzymatic polymerization, enzymatic ligation, enzymatic mismatch repair and other enzymatic functions that can be utilized in the polynucleotide assembly methods of the invention. As described above, in the invention methods of polynucleotide assembly the extended polynucleotide can be contacted with a next most terminal oligonucleotide under conditions and for such time suitable for annealing, the contacting resulting in a contiguous double-stranded polynucleotide, wherein the initiating sequence is extended. Subsequent next most terminal oligonucleotides can be added sequentially to the extended initiating polynucleotide through repeated cycles of annealing and ligation, whereby a target polynucleotide is assembled.

The polynucleotide assembly methods of the invention can include the addition of MutS during the polynucleotide assembly. MutS is a bacterial protein involved in DNA mismatch repair that recognizes and repairs numerous errors, including base mismatches, unpaired bases, and small insertion or deletion loops. MutS functions by binding the mismatched base pairs within double stranded polynucleotides and can be utilized in the methods of the invention to prevent incorporation of mismatched oligonucleotides into the extending double stranded polynucleotide. In particular, if two oligonucleotides anneal that have a single base mismatch, MutS binds to the annealed oligonucleotide and the mismatch position, thereby physically preventing the ligase enzyme to bind to and ligate adjacent oligonucleotides. As a consequence of MutS binding, oligonucleotides containing a mismatched base will not be incorporated into the extending double-stranded polynucleotide. Thus, the polynucleotide assembly methods of the invention, which include the set assembly and the sequential assembly methods described herein, can encompass addition to the reaction mixture of MutS during the, for example, the pooling or ligation steps. In the methods of polynucleotide assembly encompassing two sets of oligonucleotides provided by the invention, annealing in the presence of MutS protein the first and second sets of oligonucleotides to assemble a double-stranded polynucleotide. In general, in the sequential or set assembly methods described herein, MutS can be added to the primary reaction mixture or pool and will be present in all subsequent assembly steps.

Homologues of *Escherichia coli* MutS protein are found in almost every organism. In prokaryotes, MutS proteins originate from a single gene, while eukaryotes contain multiple mutS homologue (msh) genes. Thermostable MutS is derived from the thermophilic bacterium *Thermus aquaticus* and it has 63% identity with the *E. coli* MutS protein and 55% identity with the human homolog protein MSH2. Thermostable MutS can bind mismatched oligonucleotides at up to 70° C. and is particularly useful for practicing the claimed methods. Thermostable MutS is commercially available from a variety of sources, for example, Epicentre Technologies, Ecogen S.R.L., Madrid, Spain, and can be used according to manufacturer's instructions, for example, by adding 0.1 μg per 50 μl of reaction mix.

The polynucleotide assembly methods of the invention provide several advantages over prior art-known methods of polynucleotide synthesis. The polynucleotide assembly methods allow for assembly of large double-stranded nucleotides and eliminate the requirement for subsequent cloning and ligation into a vector that confers replication competence. Instead, the polynucleotide assembly methods of the invention enable the efficient assembly of polynucleotides of a size sufficient to encompass regulatory regions as well as distant cis- and trans-acting elements necessary for replication. Thus, the polynucleotides assembled by the methods of the invention can contain, for example, a protein coding region, promoter, translational signal, origin of replication, regulatory elements and polyadenylation signal. By providing the ability to assemble replication competent oligonucleotides due to the feasability of assembling large molecules, the invention methods allow for assembly of polynucleotides that can be directly transferred to a host cell, for example, by transformation of a bacterial host, without intermediate cloning steps.

The sequential polynucleotide assembly methods of the invention further reduce the error rate observed with methods that require hybridization of pools of large numbers of oligonucleotides. In addition, the sequential polynucleotide assembly methods of the invention can be performed with large oligonucleotides that have an overhang of about 50 percent of their length so as to result in an about 50 percent overlap upon hybridization with the corresponding complementary overhang of the extended initiating oligonucleotide. The sequential polynucleotide assembly methods of the invention eliminate the need for purification and allow for systematic assembly of identical sized double-stranded or single-stranded oligonucleotides. The assembly methods of the invention also can be performed with double-stranded or single-stranded oligonucleotides of non-identical sizes. In addition, the sequential polynucleotide assembly methods of the invention avoid mismatch problems associated with small repeated and complementary sequences encountered in traditional pooling methods.

In one embodiment, an initiating polynucleotide of the invention can be bound to a solid support for improved efficiency. The solid phase allows for the efficient separation of the assembled target polynucleotide from other components of the reaction. Different supports can be applied in the method. For example, supports can be magnetic latex beads or magnetic control pore glass beads that allows the desirable product from the reaction mixture to be magnetically separated. Binding the initiating polynucleotide to such beads can be accomplished by a variety of known methods, for example carbodiimide treatment (Gilham, Biochemistry 7:2809–2813 (1968); Mizutani and Tachbana, J. Chromatography 356:202–205 (1986); Wolf et al., Nucleic Acids Res. 15:2911–2926 (1987); Musso, Nucleic Acids Res. 15:5353–5372 (1987); Lund et al., Nucleic Acids Res. 16:10861–10880 (1988)).

The initiating polynucleotide attached to the solid phase can act as an anchor for the continued synthesis of the target polynucleotide. Assembly can be accomplished by addition of contiguous polynucleotides together with ligase for ligation assembly or by addition of oligonucleotides together with polymerase for primer extension assembly. After the appropriate incubation time, unbound components of the method can be washed out and the reaction can be repeated again to improve the efficiency of template utilization. Alternatively, another set of polynucleotides or oligonucleotides can be added to continue the assembly.

Solid phase, to be efficiently used for the synthesis, can contain pores with sufficient room for synthesis of the long nucleic acid molecules. The solid phase can be composed of material that cannot non-specifically bind any undesired components of the reaction. One way to solve the problem is to use control pore glass beads appropriate for long DNA molecules. The initiating polynucleotide can be attached to the beads through a long connector. The role of the connector is to position the initiating polynucleotide from the surface of the solid support at a desirable distance.

The method of the invention further includes identifying a next most terminal oligonucleotide present in the target polynucleotide, which is contiguous with the initiating polynucleotide. A next most terminal oligonucleotide can include at least one plus strand oligonucleotide annealed to at least one minus strand oligonucleotide resulting in a partially double-stranded oligonucleotide nucleotide comprising a 5' overhang, a 3' overhang, or a 5' overhang and a 3' overhang, where at least one overhang of the next most terminal oligonucleotide is complementary to at least one overhang of the extended initiating polynucleotide. Alternatively, a next most terminal oligonucleotide can be single-stranded and include a region, referred to as an overhang herein, complementary to at least one overhang of the extended initiating polypeptide. Two or more oligonucleotides having complementary regions, where they are permitted, will "anneal" (i.e., base pair) under the appropriate conditions, thereby producing a double-stranded region. In order to anneal (i.e., hybridize), oligonucleotides must be at least partially complementary. The term "complementary to" is used herein in relation to nucleotides to mean a nucleotide that will base pair with another specific nucleotide. Thus adenosine triphosphate is complementary to uridine triphosphate or thymidine triphosphate and guanosine triphosphate is complementary to cytidine triphosphate.

As used herein, a 5' or 3' "overhang" means a single-stranded region on the 5' or 3', or 5' and 3', end of a double-stranded or single-stranded polynucleotide or of a double-stranded or single-stranded oligonucleotide that provides a means for the subsequent annealing of a contiguous polynucleotide or oligonucleotide containing an overhang that is complementary to the overhang of the contiguous polynucleotide or oligonucleotide. Depending on the application envisioned, one will desire to employ varying conditions of annealing to achieve varying degrees of annealing selectivity.

For applications requiring high selectivity, one typically will desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the oligonucleotide and the template or target strand. It generally is appreciated that conditions can be rendered more stringent by the addition of increasing amounts of formamide.

For certain applications, for example, by analogy to substitution of nucleotides by site-directed mutagenesis, it is appreciated that lower stringency conditions can be used. Under these conditions, hybridization can occur even though the sequences of probe and target strand are not perfectly complementary, but are mismatched at one or more positions. Conditions can be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

In certain embodiments, it will be advantageous to determine the hybridization of oligonucleotides by employing a label. A wide variety of appropriate labels are known in the art, including fluorescent, radioactive, enzymatic or other ligands, such as avidin/biotin, which are capable of being detected. In preferred embodiments, one can desire to employ a fluorescent label or an enzyme tag such as urease, alkaline phosphatase or peroxidase, instead of radioactive or other environmentally undesirable reagents. In the case of enzyme tags, calorimetric indicator substrates are known that can be employed to provide a means for detection visible to the human eye or spectrophotometrically to identify whether specific hybridization with complementary oligonucleotide has occurred.

In embodiments involving a solid phase, for example, at least one oligonucleotide of an initiating polynucleotide is adsorbed or otherwise affixed to a selected matrix or surface. This fixed, single-stranded nucleic acid is then subjected to hybridization with the complementary oligonucleotides under desired conditions. The selected conditions will also depend on the particular circumstances based on the particular criteria required (depending, for example, on the G+C content, type of target nucleic acid, source of nucleic acid, size of hybridization probe, etc.). Following washing of the hybridized surface to remove non-specifically bound oligonucleotides, the hybridization can be detected, or even quantified, by means of the label.

In one embodiment, the method of the invention further includes identifying a second polynucleotide sequence present in the target polynucleotide which is contiguous with the initiating polynucleotide and includes at least one plus strand oligonucleotide annealed to at least one minus strand oligonucleotide resulting in a partially double-stranded polynucleotide comprised of a 5' overhang, a 3' overhang, or a 5' overhang and a 3' overhang, where at least one overhang of the second polynucleotide is complementary to at least one overhang of the initiating polynucleotide. In this embodiment, the invention further provides a third polynucleotide present in the target polynucleotide which is contiguous with the initiating sequence and provides a 5' overhang, a 3' overhang, or a 5' overhang and a 3' overhang, where at least one overhang of the third polynucleotide is complementary to at least one overhang of the initiating polynucleotide which is not complementary to an overhang of the second polynucleotide. Subsequent polynucleotides are added at alternating ends so as to extend the initiating polynucleotide in an alternating bi-directional manner.

The method further provides contacting the initiating polynucleotide with the second polynucleotide and the third polynucleotide under conditions and for such time suitable for annealing, the contacting resulting in a contiguous double-stranded polynucleotide, resulting in the extension of the initiating polynucleotide. The annealed polynucleotides are optionally contacted with a ligase under conditions suitable for ligation. The method discussed above is optionally repeated to sequentially add double-stranded polynucleotides to the extended initiating polynucleotide through repeated cycles of annealing and ligation.

As described herein, in the methods of the invention the intitiating polynucleotide can be extended by uni-directional or by bi-directional extension as well as by mixed uni-directional and bi-directional extension. As described above, in an alternating bi-directional extension a next most terminal oligonucleotide or polynucleotide is added that has least one overhang complementary to at least one overhang of the extended initiating polynucleotide which is not complementary to an overhang of the oligonucleotide or polynucleotide that was added immediately before, thus resulting in an alternating bi-directional pattern of addition of subsequent next most terminal oligonucleotides. In other embodiments, a next most terminal oligonucleotide can be any next most terminal polynucleotide regardless of whether its addition to the extending double-stranded polynucleotide will result in bi-directional or uni-directional extension. In such embodiments, the next most terminal oligonucleotide or polynucleotide has an overhang that can be complementary to any overhang of the extending double-stranded polynucleotide.

According to the methods of the invention a polynucleotide can be assembled randomly or can encompass target polynucleotide sequence, which can be designed de novo or derived from a predetermined model polynucleotide sequence. A target polynucleotide can be of any desired size or complexity and can include anything from polyncleotides encoding entire genomes or pathways to partial sequences, segments or fragments of an oligonucleotide or polynucleotide. A model polynucleotide sequence includes any nucleic acid sequence that is predetermined before assembly and, for example, can encode a model polypeptide sequence. A model polypeptide sequence can provide a basis for designing a modified polynucleotide such that a target polynucleotide incorporating the desired modification is synthesized.

The present invention provides also provides methods that can be used to synthesize, de novo, polynucleotides that encode sets of genes, either naturally occurring genes expressed from natural or artificial promoter constructs or artificial genes derived from synthetic DNA sequences, which encode elements of biological systems that perform a specified function or attribution of an artificial organism as well as entire genomes. In producing such systems and genomes, the present invention provides the synthesis of a replication-competent, double-stranded polynucleotide, wherein the polynucleotide has an origin of replication, a first coding region and a first regulatory region directing the expression of the first coding region.

As used herein, the term "replication-competent", refers to a polynucleotide that is capable of directing its own replication. A replication-competent polynucleotide encompasses a regulatory region that has the cis-acting signals and regulatory elements required to direct expression of the coding region. The replication-competent polynucleotide obviates the need for recombinant methods such as cloning of a synthesized coding region into a vector such as a plasmid or a virus in order to confer replication-competence.

A polynucleotide sequence defining a gene, genome, set of genes or protein sequence can be designed in a computer-assisted manner (discussed below) and used to generate a set of parsed oligonucleotides covering the plus (+) and minus (−) strand of the sequence. As used herein, a "parsed" means a target polynucleotide sequence has been delineated in a computer-assisted manner such that a series of contiguous oligonucleotide sequences are identified. The oligonucleotide sequences are individually synthesized and used in a method of the invention to generate a target polynucleotide. The length of an oligonucleotide is quite variable. Preferably, oligonucleotides used in the methods of the invention are between about 15 and 100 bases and more preferably between about 20 and 50 bases. Specific lengths include, but are not limited to 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 bases. Depending on the size, the overlap between the oligonucleotides having partial complementarity can be designed to be between 5 and 75 bases per oligonucleotide pair.

The oligonucleotides preferably are treated with polynucleotide kinase, for example, T4 polynucleotide kinase. The kinasing can be performed prior to, or after, mixing of the oligonucleotides set or after, but before annealing. After annealing, the oligonucleotides are treated with an enzyme having a ligating function. For example, a DNA ligase typically will be employed for this function. However, topoisomerase, which does not require 5' phosphorylation, is rapid and operates at room temperature, and can be used instead of ligase. For example, 50 base pair oligonucleotides overlapping by 25 bases can be synthesized by an oligonucleotide array synthesizer (OAS). A 5' (+) strand set of oligonucleotides is synthesized in one 96-well plate and the second 3' or (−) strand set is synthesized in a second 96-well microtiter plate. Synthesis can be carried out using phosphoramidite chemistry modified to miniaturize the reaction size and generate small reaction volumes and yields in the range of 2 to 5 nmole. Synthesis is done on controlled pore glass beads (CPGs), then the completed oligonucleotides are deblocked, deprotected and removed from the beads. The oligonucleotides are lyophilized, re-suspended in water and 5' phosphorylated using polynucleotide kinase and ATP to enable ligation.

The set of arrayed oligonucleotide sequences in the plate can be assembled using a mixed pooling strategy. For example, systematic pooling of component oligonucleotides can be performed using a modified Beckman Biomek automated pipetting robot, or another automated lab workstation. The fragments can be combined with buffer and enzyme (Taq I DNA ligase or Egea Assemblase™, for example). Pooling can be performed in microwell plates. After each step of pooling, the temperature is ramped to enable annealing and ligation, then additional pooling carried out.

In the assembly methods of the invention, slow annealing by generally no more than 1.5° C. per minute to 37° C. or below can performed to maximize the efficiency of hybridization. Slow annealing can be accomplished by a variety of methods, for example, with a programmable thermocycler. The cooling rate can be linear or non-linear and can be, for example, 0.1° C., 0.2° C., 0.3° C., 0.4° C., 0.5° C., 0.6° C., 0.7° C., 0.8° C., 0.9° C., 1.0° C., 1.1° C., 1.2° C., 1.3° C., 1.4° C., 1.5° C., 1.6° C., 1.7° C., 1.8° C., 1.9° C., or 2.0° C. The cooling rate can be adjusted up or down to maximize efficiency and accuracy.

Target polynucleotide assembly involves forming a set of intermediates. A set of intermediates can include a plus strand oligonucleotide annealed to a minus strand oligonucleotide, as described above. The annealed intermediate can be formed by providing a single plus strand oligonucleotide annealed to a single minus strand oligonucleotide.

Alternatively, two or more oligonucleotides can comprise the plus strand or the minus strand. For example, in order to construct a polynucleotide (e.g., an initiating polynucleotide) which can be used to assemble a target polynucleotide of the invention, three or more oligonucleotides can be annealed. Thus, a first plus strand oligonucleotide, a second plus strand oligonucleotide contiguous with the first plus strand oligonucleotide, and a minus strand oligonucleotide having a first contiguous sequence which is at least partially complementary to the first plus strand oligonucleotide and second contiguous sequence which is at least partially complementary to the second plus strand oligonucleotide can be annealed to form a partially double-stranded polynucleotide. The polynucleotide can include a 5' overhang, a 3' overhang, or a 5' overhang and a 3' overhang. The first plus strand oligonucleotide and second plus strand oligonucleotide are contiguous sequences such that they are ligatable. The minus strand oligonucleotide is partially complementary to both plus strand oligonucleotides and acts as a "bridge" or "stabilizer" sequence by annealing to both oligonucleotides. Subsequent polynucleotides comprised of more than two oligonucleotides annealed as previously described, can be used to assemble a target polynucleotide in a manner resulting in a contiguous double-stranded polynucleotide.

Figure 3:
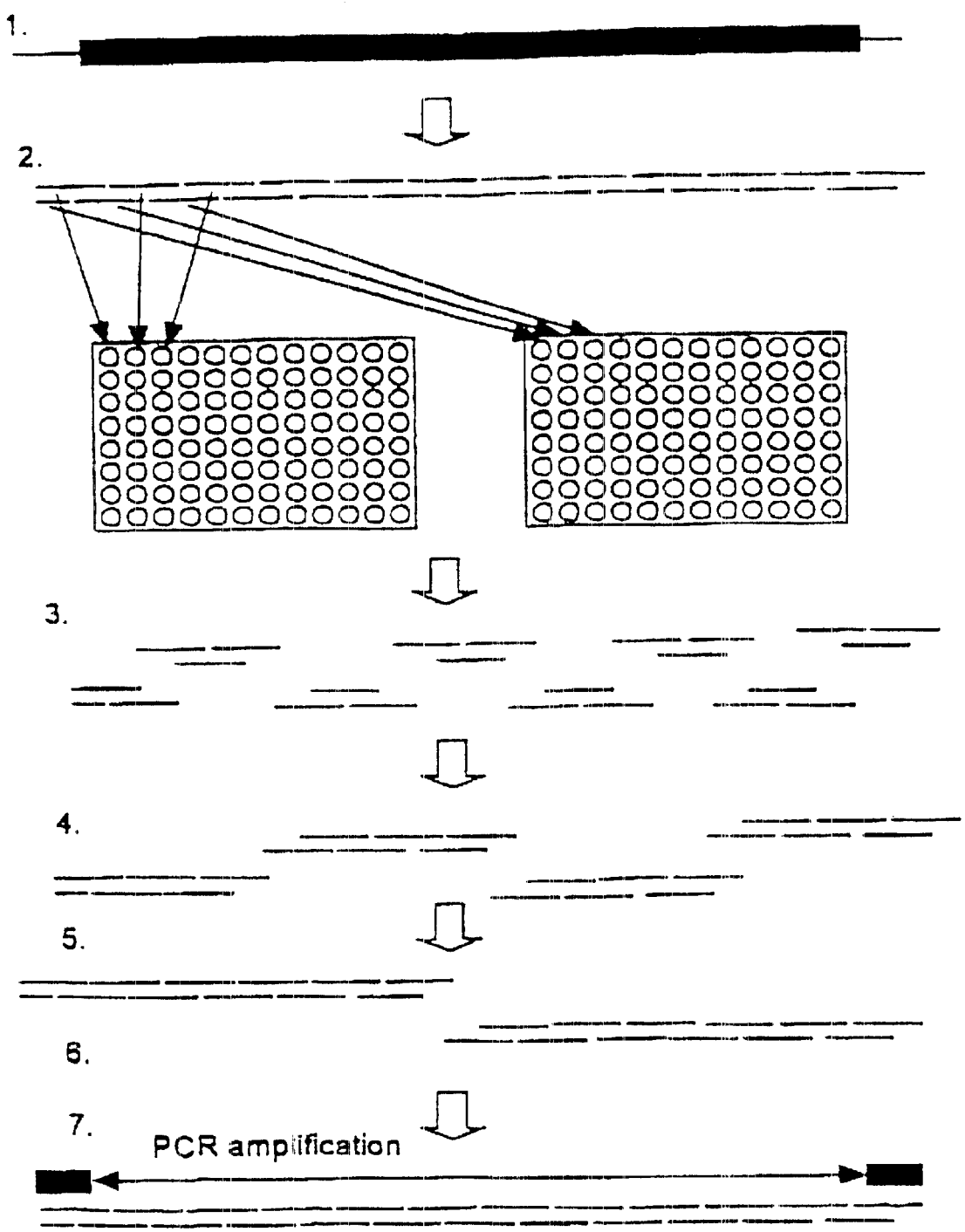
FIG. 3 depicts the schematic of assembly of a target polynucleotide sequence defining a gene, genome, set of genes or polypeptide sequence. The sequence is designed by computer and used to generate a set of parsed oligonucleotide fragments covering the + and − strand of a target polynucleotide sequence encoding a target polypeptide.

An example of using two or more plus strand oligonucleotides to assemble a polynucleotide is shown in FIG. 3. A triplex of three oligonucleotides of about 50 bp each, which overlap by about 25 bp form a "nicked" intermediate. Two of these oligonucleotides provide a ligation substrate joined by ligase and the third oligonucleotide is a stabilizer that brings together two specific sequences by annealing resulting in the formation of a part of the final polynucleotide construct. This intermediate provides a substrate for DNA ligase which, through its nick sealing activity, joins the two 50-base pair oligonucleotides into a single 100 base single-stranded polynucleotide.

Following initial pooling and formation of annealed products, the products are assembled into increasingly larger polynucleotides. For example, following triplex formation of oligonucleotides, sets of triplexes are systematically joined, ligated, and assembled. Each step can be mediated by robotic pooling, ligation and thermal cycling to achieve annealing and denaturation. The final step joins assembled pieces into a complete sequence representing all of the fragments in the array. Since the efficiency of yield at each step is less than 100%, the mass amount of completed product in the final mixture can be very small. Optionally, additional specific oligonucleotide primers, usually 15 to 20 bases and complementary to the extreme ends of the assembly, can be annealed and PCR amplification carried out, thereby amplifying and purifying the final full-length product.

The methods of the invention provide several improvements over existing polynucleotide synthesis technology. For example, synthesis can utilize microdispensing piezioelectric or microsolenoid nanodispensors allowing very fast synthesis, much smaller reaction volumes and higher density plates as synthesis vessels. The instrument will use up to 1536 well plates giving a very high capacity. Additionally, controlled pooling can be performed by a microfluidic manifold that will move individual oligonucleotides though microchannels and mix/ligate in a controlled way. This will obviate the need for robotic pipetting and increases speed and efficiency. Thus, an apparatus that accomplishes a method of the invention will have a greater capability for simultaneous reactions giving an overall larger capacity for gene length.

Once target polynucleotides have been synthesized using a method of the present invention, it can be necessary to screen the sequences for analysis of function. Specifically contemplated by the present inventor are chip-based DNA technologies. Briefly, these techniques involve quantitative methods for analyzing large numbers of genes rapidly and accurately. By tagging genes with oligonucleotides or using fixed probe arrays, one can employ chip technology to segregate target molecules as high-density arrays and screen these molecules on the basis of hybridization.

The use of combinatorial synthesis and high throughput screening assays are well known to those of skill in the art. For example, U.S Pat. No. 5,807,754; 5,807,683; 5,804,563; 5,789,162; 5,783,384; 5,770,358; 5,759,779; 5,747,334; 5,686,242; 5,198,346; 5,738,996; 5,733,743; 5,714,320; and 5,663,046 (each specifically incorporated herein by reference) describe screening systems useful for determining the activity of a target polypeptide. These patents teach various aspects of the methods and compositions involved in the assembly and activity analyses of high-density arrays of different polysubunits (polynucleotides or polypeptides). As such it is contemplated that the methods and compositions described in the patents listed above can be useful in assaying the activity profiles of the target polypeptides of the present invention.

In another embodiment, the invention provides a method of synthesizing a target polynucleotide by providing a target polynucleotide sequence and identifying at least one initiating polynucleotide sequence present in the target polynucleotide sequence that includes at least one plus strand oligonucleotide annealed to at least one minus strand oligonucleotide resulting in a double-stranded polynucleotide. The initiating polynucleotide is contacted under conditions suitable for primer annealing with a first oligonucleotide having partial complementarity to the 3' portion of the plus strand of the initiating polynucleotide, and a second oligonucleotide having partial complementarity to the 3' portion of the minus strand of the initiating polynucleotide. Primer extension subsequently performed using polynucleotide synthesis from the 3'-hydroxyl of: 1) the plus strand of the initiating polynucleotide; 2) the annealed first oligonucleotide; 3) the minus strand of the initiating polynucleotide; and 4) the annealed second oligonucleotide. The synthesis results in the initiating sequence being extended bi-directionally thereby forming a nascent extended initiating polynucleotide. The extended initiating sequence can be further extended by repeated cycles of annealing and primer extension.

As previously noted, oligonucleotides can be used as building blocks to assemble polynucleotides through annealing and ligation reactions. Alternatively, oligonucleotides can be used as primers to manufacture polynucleotides through annealing and primer extension reactions. The term "primer" is used herein to refer to a binding element which comprises an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of appropriate nucleotides and an agent for polymerization such as a DNA polymerase in an appropriate buffer ("buffer" includes pH, ionic strength, cofactors, etc.) and at a suitable temperature.

The primer is preferably single stranded for maximum efficiency in amplification, but can alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primer and use of the method. Primers having only short sequences capable of hybridization to the target nucleotide sequence generally require lower temperatures to form sufficiently stable hybrid complexes with the template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. Commonly, however, the primers have exact complementarity except with respect to analyses effected according to the method described in Nucleic Acids Research 17 (7) 2503–2516 (1989) or a corresponding method employing linear amplification or an amplification technique other than the polymerase chain reaction.

The agent for primer extension of an oligonucleotide can be any compound or system that will function to accomplish the synthesis of primer extension products, including enzymes. Suitable enzymes for this purpose include, for example, *E. coli* DNA Polymerase I, Klenow fragment of *E. coli* DNA polymerase I, T4 DNA polymerase, other available DNA polymerases, reverse transcriptase, and other enzymes, including thermostable enzymes. The term "thermostable enzyme" as used herein refers to any enzyme that is stable to heat and is heat resistant and catalyses (facilitates) combination of the nucleotides in the proper manner to form the primer extension products which are complementary to each nucleic acid strand. Generally, the synthesis will be initiated at the 3' end of each primer and will proceed in the 5' direction along the template strand, until synthesis terminates. A preferred thermostable enzyme that can be employed in the process of the present invention is that which can be extracted and purified from *Thermus aquaticus*. Such an enzyme has a molecular weight of about 86,000–90,000 daltons. Thermus aquaticus strain YT1 is available without restriction from the American Type Culture Collection, 12301 Parklawn Drive, Rockville, Md., U.S.A. as ATCC 25,104.

Processes for amplifying a desired target polynucleotide are known and have been described in the literature. K. Kleppe et al in J. Mol. Biol., (1971), 56, 341–361 disclose a method for the amplification of a desired DNA sequence. The method involves denaturation of a DNA duplex to form single strands. The denaturation step is carried out in the presence of a sufficiently large excess of two nucleic acid primers that hybridize to regions adjacent to the desired DNA sequence. Upon cooling two structures are obtained each containing the full length of the template strand appropriately complexed with primer. DNA polymerase and a sufficient amount of each required nucleoside triphosphate are added whereby two molecules of the original duplex are obtained. The above cycle of denaturation, primer addition and extension are repeated until the appropriate number of copies of the desired target polynucleotide is obtained.

The present invention further provides a method for the expression and isolation of a target polypeptide encoded by a target polynucleotide. The method includes incorporating a target polynucleotide synthesized by a method of the invention into an expression vector; introducing the expression vector of into a suitable host cell; culturing the host cell under conditions and for such time as to promote the expression of the target polypeptide encoded by the target polynucleotide; and isolating the target polypeptide.

The invention can be used to modify certain functional, structural, or phylogenic features of a model polynucleotide encoding a model polypeptide resulting in an altered target polypeptide. An input or model polynucleotide sequence encoding a model polypeptide can be electronically manipulated to determine a potential for an effect of an amino acid change (or variance) at a particular site or multiple sites in the model polypeptide. Once identified, a novel target polynucleotide sequence is assembled by a method of the invention such that the target polynucleotide encodes a target polypeptide possessing a characteristic different from that of the model polypeptide.

The methods of the invention can rely on the use of public sequence and structure databases. These databases become more robust as more and more sequences and structures are added. Information regarding the amino acid sequence of a target polypeptide and the tertiary structure of the polypeptide can be used to synthesize oligonucleotides that can be assembled into a target polynucleotide encoding a target polypeptide. A model polypeptide should have sufficient structural information to analyze the amino acids involved in the function of the polypeptide. The structural information can be derived from x-ray crystallography, NMR, or some other technique for determining the structure of a protein at the amino acid or atomic level. Once selected, the sequence and structural information obtained from the model polypeptide can be used to generate a plurality of polynucleotides encoding a plurality of variant amino acid sequences that comprise a target polypeptide. Thus, a model polypeptide can be selected based on overall sequence similarity to the target protein or based on the presence of a portion having sequence similarity to a portion of the target polypeptide.

A "polypeptide", as used herein, is a polymer in which the monomers are alpha amino acids and are joined together through amide bonds. Amino acids can be the L-optical isomer or the D-optical isomer. Polypeptides are two or more amino acid monomers long and are often more than 20 amino acid monomers long. Standard abbreviations for amino acids are used (e.g., P for proline). These abbreviations are included in Stryer, Biochemistry, Third Ed., 1988, which is incorporated herein by reference for all purposes. With respect to polypeptides, "isolated" refers to a polypeptide that constitutes the major component in a mixture of components, e.g., 50% or more, 60% or more, 70% or more, 80% or more, 90% or more, or 95% or more by weight. Isolated polypeptides typically are obtained by purification from an organism in which the polypeptide has been produced, although chemical synthesis is also possible. Method of polypeptide purification includes, for example, chromatography or immunoaffinity techniques. Polypeptides of the invention can be detected by sodium dodecyl sulphate (SDS)-polyacrylamide gel electrophoresis followed by Coomassie Blue-staining or Western blot analysis using monoclonal or polyclonal antibodies that have binding affinity for the polypeptide to be detected.

A "chimeric polypeptide," as used herein, is a polypeptide containing portions of amino acid sequence derived from two or more different proteins, or two or more regions of the same protein that are not normally contiguous.

A "ligand", as used herein, is a molecule that is recognized by a receptor. Examples of ligands that can be investigated by this invention include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, and proteins.

A "receptor", as used herein, is a molecule that has an affinity for a ligand. Receptors can be naturally-occurring or manmade molecules. They can be employed in their unaltered state or as aggregates with other species. Receptors can be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, and organelles. A "ligand receptor pair" is formed when two molecules have combined through molecular recognition to form a complex.

Specific examples of polypeptides which can synthesized by this invention include but are not restricted to:
  a) Microorganism receptors: Determination of ligands that bind to microorganism receptors such as specific transport proteins or enzymes essential to survival of microorganisms would be a useful tool for discovering new classes of antibiotics. Of particular value would be antibiotics against opportunistic fungi, protozoa, and bacteria resistant to antibiotics in current use.
  b) Enzymes: For instance, a receptor can comprise a binding site of an enzyme such as an enzyme responsible for cleaving a neurotransmitter; determination of ligands for this type of receptor to modulate the action of an enzyme that cleaves a neurotransmitter is useful in developing drugs that can be used in the treatment of disorders of neurotransmission.

c) Antibodies: For instance, the invention can be useful in investigating a receptor that comprises a ligand-binding site on an antibody molecule which combines with an epitope of an antigen of interest; determining a sequence that mimics an antigenic epitope can lead to the development of vaccines in which the immunogen is based on one or more of such sequences or lead to the development of related diagnostic agents or compounds useful in therapeutic treatments such as for autoimmune diseases (e.g., by blocking the binding of the "self" antibodies).

d) Polynucleotides: Sequences of polynucleotides can be synthesized to establish DNA or RNA binding sequences that act as receptors for synthesized sequence.

e) Catalytic Polypeptides: Polymers, preferably antibodies, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant. Catalytic polypeptides and others are described in, for example, PCT Publication No. WO 90/05746, WO 90/05749, and WO 90/05785, which are incorporated herein by reference for all purposes.

f) Hormone receptors: Identification of the ligands that bind with high affinity to a receptor such as the receptors for insulin and growth hormone is useful in the development of, for example, an oral replacement of the daily injections which diabetics must take to relieve the symptoms of diabetes or a replacement for growth hormone. Other examples of hormone receptors include the vasoconstrictive hormone receptors; determination of ligands for these receptors can lead to the development of drugs to control blood pressure.

g) Opiate receptors: Determination of ligands which bind to the opiate receptors in the brain is useful in the development of less-addictive replacements for morphine and related drugs.

In the context of a polypeptide, the term "structure" refers to the three dimensional arrangement of atoms in the protein. "Function" refers to any measurable property of a protein. Examples of protein function include, but are not limited to, catalysis, binding to other proteins, binding to non-protein molecules (e.g., drugs), and isomerization between two or more structural forms. "Biologically relevant protein" refers to any protein playing a role in the life of an organism.

To identify significant structural motifs, the sequence of the model polypeptide is examined for matches to the entries in one or more databases of recognized domains, e.g., the PROSITE database domains (Bairoch, Nucl. Acids. Res. 24:217, 1997) or the pfam HMM database (Bateman et al., (2000) Nucl. Acids. Res. 28:263). The PROSITE database is a compilation of two types of sequence signatures-profiles, typically representing whole protein domains, and patterns typically representing just the most highly conserved functional or structural aspects of protein domains.

The methods of the invention can be used to generate polypeptides containing polymorphisms that have an effect on a catalytic activity of a target polypeptide or a non-catalytic activity of the target polypeptide (e.g., structure, stability, binding to a second protein or polypeptide chain, binding to a nucleic acid molecule, binding to a small molecule, and binding to a macromolecule that is neither a protein nor a nucleic acid). For example, the invention provides a means for assembling any polynucleotide sequence encoding a target polypeptide such that the encoded polypeptide can be expressed and screened for a particular activity. By altering particular amino acids at specific points in the target polypeptide, the operating temperature, operating pH, or any other characteristic of a polypeptide can be manipulated resulting in a polypeptide with a unique activity. Thus, the methods of the invention can be used to identify amino acid substitutions that can be made to engineer the structure or function of a polypeptide of interest (e.g., to increase or decrease a selected activity or to add or remove a selective activity).

In addition, the methods of the invention can be used in the identification and analysis of candidate polymorphisms for polymorphism-specific targeting by pharmaceutical or diagnostic agents, for the identification and analysis of candidate polymorphisms for pharmacogenomic applications, and for experimental biochemical and structural analysis of pharmaceutical targets that exhibit amino acid polymorphism.

A library of target polynucleotides encoding a plurality of target polypeptides can be prepared by the present invention. Host cells are transformed by artificial introduction of the vectors containing the target polynucleotide by inoculation under conditions conducive for such transformation. The resultant libraries of transformed clones are then screened for clones which display activity for the polypeptide of interest in a phenotypic assay for activity.

A target polynucleotide of the invention can be incorporated (i.e., cloned) into an appropriate vector. For purposes of expression, the target sequences encoding a target polypeptide of the invention can be inserted into a recombinant expression vector. The term "recombinant expression vector" refers to a plasmid, virus, or other vehicle known in the art that has been manipulated by insertion or incorporation of the polynucleotide sequence encoding a target polypeptide of the invention. The expression vector typically contains an origin of replication, a promoter, as well as specific genes that allow phenotypic selection of the transformed cells. Vectors suitable for use in the present invention include, but are not limited to, the T7-based expression vector for expression in bacteria (Rosenberg et al., Gene, 56:125, 1987), the pMSXND expression vector for expression in mammalian cells (Lee and Nathans, J. Biol. Chem., 263:3521, 1988), baculovirus-derived vectors for expression in insect cells, cauliflower mosaic virus, CaMV, tobacco mosaic virus, TMV.

Depending on the vector utilized, any of a number of suitable transcription and translation elements, including constitutive and inducible promoters, transcription enhancer elements, transcription terminators, etc. can be used in the expression vector (see, e.g., Bitter et al., Methods in Enzymology, 153:516–544, 1987). These elements are well known to one of skill in the art.

The term "operably linked" or "operably associated" refers to functional linkage between the regulatory sequence and the polynucleotide sequence regulated by the regulatory sequence. The operably linked regulatory sequence controls the expression of the product expressed by the polynucleotide sequence. Alternatively, the functional linkage also includes an enhancer element.

"Promoter" means a nucleic acid regulatory sequence sufficient to direct transcription. Also included in the invention are those promoter elements that are sufficient to render promoter-dependent polynucleotide sequence expression controllable for cell-type specific, tissue specific, or inducible by external signals or agents; such elements can be located in the 5' or 3' regions of the native gene, or in the introns.

"Gene expression" or "polynucleotide sequence expression" means the process by which a nucleotide sequence undergoes successful transcription and translation such that detectable levels of the delivered nucleotide sequence are expressed in an amount and over a time period so that a functional biological effect is achieved.

In yeast, a number of vectors containing constitutive or inducible promoters can be used. (Current Protocols in Molecular Biology, Vol. 2, Ed. Ausubel et al., Greene Publish. Assoc. & Wiley Interscience, Ch. 13, 1988; Grant et al., "Expression and Secretion Vectors for Yeast," in Methods in Enzymology, Eds. Wu & Grossman, Acad. Press, N.Y., Vol. 153, pp.516–544, 1987; Glover, DNA Cloning, Vol. II, IRL Press, Wash., D.C., Ch. 3, 1986; "Bitter, Heterologous Gene Expression in Yeast," Methods in Enzymology, Eds. Berger & Kimmel, Acad. Press, N.Y., Vol. 152, pp. 673–684, 1987; and The Molecular Biology of the Yeast Saccharomyces, Eds. Strathern et al., Cold Spring Harbor Press, Vols. I and II, 1982). A constitutive yeast promoter, such as ADH or LEU2, or an inducible promoter, such as GAL, can be used ("Cloning in Yeast," Ch. 3, R. Rothstein In: DNA Cloning Vol.11, A Practical Approach, Ed. DM Glover, IRL Press, Wash., D.C., 1986). Alternatively, vectors can be used which promote integration of foreign DNA sequences into the yeast chromosome.

In certain embodiments, it can be desirable to include specialized regions known as telomeres at the end of a target polynucleotide sequence. Telomeres are repeated sequences found at chromosome ends and it has long been known that chromosomes with truncated ends are unstable, tend to fuse with other chromosomes and are otherwise lost during cell division.

Some data suggest that telomeres interact with the nucleoprotein complex and the nuclear matrix. One putative role for telomeres includes stabilizing chromosomes and shielding the ends from degradative enzyme.

Another possible role for telomeres is in replication. According to present doctrine, replication of DNA requires starts from short RNA primers annealed to the T-end of the template. The result of this mechanism is an "end replication problem" in which the region corresponding to the RNA primer is not replicated. Over many cell divisions, this will result in the progressive truncation of the chromosome. It is thought that telomeres can provide a buffer against this effect, at least until they are themselves eliminated by this effect. A further structure that can be included in target polynucleotide is a centromere.

In certain embodiments of the invention, the delivery of a nucleic acid in a cell can be identified in vitro or in vivo by including a marker in the expression construct. The marker would result in an identifiable change to the transfected cell permitting easy identification of expression.

An expression vector of the invention can be used to transform a target cell. By "transformation" is meant a genetic change induced in a cell following incorporation of new DNA (i.e., DNA exogenous to the cell). Where the cell is a mammalian cell, the genetic change is generally achieved by introduction of the DNA into the genome of the cell. By "transformed cell" is meant a cell into which (or into an ancestor of which) has been introduced, by means of recombinant DNA techniques. Transformation of a host cell with recombinant DNA can be carried out by conventional techniques as are well known to those skilled in the art. Where the host is prokaryotic, such as E. coli, competent cells that are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

A target polypeptide of the invention can be produced in prokaryotes by expression of nucleic acid encoding the polypeptide. These include, but are not limited to, microorganisms, such as bacteria transformed with recombinant bacteriophage DNA, plasmid DNA, or cosmid DNA expression vectors encoding a polypeptide of the invention. The constructs can be expressed in E. coli in large scale for in vitro assays. Purification from bacteria is simplified when the sequences include tags for one-step purification by nickel-chelate chromatography. The construct can also contain a tag to simplify isolation of the polypeptide. For example, a polyhistidine tag of, e.g., six histidine residues, can be incorporated at the amino terminal end, or carboxy terminal end, of the protein. The polyhistidine tag allows convenient isolation of the protein in a single step by nickel-chelate chromatography. The target polypeptide of the invention can also be engineered to contain a cleavage site to aid in protein recovery. Alternatively, the polypeptides of the invention can be expressed directly in a desired host cell for assays in situ.

When the host is a eukaryote, such methods of transfection of DNA as calcium phosphate co-precipitates, conventional mechanical procedures, such as microinjection, electroporation or biollistic techniques, insertion of a plasmid encased in liposomes, or virus vectors can be used. Eukaryotic cells can also be cotransfected with DNA sequences encoding a polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell, as described herein. Eukaryotic systems, and preferably mammalian expression systems, allow for proper post-translational modifications of expressed mammalian proteins to occur. Eukaryotic cells that possess the cellular machinery for proper processing of the primary transcript, glycosylation, phosphorylation, and advantageously secretion of the gene product should be used as host cells for the expression of the polypeptide of the invention. Such host cell lines can include, but are not limited to, CHO, VERO, BHK, HeLa, COS, MDCK, Jurkat, HEK-293, and WI38.

For long-term, high-yield production of recombinant proteins, stable expression is preferred. Rather than using expression vectors that contain viral origins of replication, host cells can be transformed with the cDNA encoding a target polypeptide of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci that, in turn, can be cloned and expanded into cell lines. For example, following the introduction of foreign DNA, engineered cells can be allowed to grow for 1–2 days in an enriched media, and then are switched to a selective media. A number of selection systems can be used, including, but not limited to, the herpes simplex virus thymidine kinase (Wigler et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy et al., Cell, 22:817, 1980) genes can be employed in tk-, hgprt- or aprt-cells, respectively. Also, antimetabolite resistance can be used as the basis of selection for dhfr, which confers resistance to methotrexate (Wigler et al., Proc. Natl. Acad. Sci. USA, 77:3567, 1980; O'Hare et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin et al., J. Mol. Biol., 150:1, 1981); and hygro, which confers resistance to hygromycin genes (Santerre et al., Gene, 30:147, 1984). Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase), which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

Techniques for the isolation and purification of either microbially or eukaryotically expressed polypeptides of the invention can be by any conventional means, such as, for example, preparative chromatographic separations and immunological separations, such as those involving the use of monoclonal or polyclonal antibodies or antigen.

A target polynucleotide, or expression construct containing a target polynucleotide, can be entrapped in a liposome. Liposomes are vesicular structures characterized by a phospholipid bilayer membrane and an inner aqueous medium. Multilarnellar liposomes have multiple lipid layers separated by aqueous medium and form spontaneously when phospholipids are suspended in an excess of aqueous solution. The lipid components undergo self-rearrangement before the formation of closed structures and entrap water and dissolved solutes between the lipid bilayers. The liposome can be complexed with a hernagglutinating virus (HVJ). This has been shown to facilitate fusion with the cell membrane and promote cell entry of liposome-encapsulated DNA. In other embodiments, the liposome can be complexed or employed in conjunction with nuclear non-histone chromosomal proteins (HMG-1). In yet further embodiments, the liposome can be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

The present invention describes methods for enabling the creation of a target polynucleotide based upon information only, i.e., without the requirement for existing genes, DNA molecules or genomes. Generally, using computer software, it is possible to construct a virtual polynucleotide in the computer. This polynucleotide consists of a string of DNA bases, G, A, T or C, comprising for example an entire artificial polynucleotide sequence in a linear string. Following construction of a sequence, computer software is then used to parse the target sequence breaking it down into a set of overlapping oligonucleotides of specified length. Optional steps in sequence assembly include identifying and eliminating sequences that may give rise to hairpins, repeats or other sequences that are undesirable. Therefore, success in a large gene construction can be substantially improved by pre-screening sequences for difficult regions or areas. In short, an amino acid sequence is used to generate a synthetic gene sequence using *E. coli* class II codons. Prior ti sequence parsing, a number of subroutines are applied to the sequence to identify specific types of sequences arrangements that could cause early termination in oligo synthesis, difficult or low efficiency in ligation or synthesis, unusual or atypical secondary structures. Programs are used to analyze the sequence and identify:

Any region of over 25 base pairs with a GC content of over 70%

Any 3' or 5' terminal sequences that would form a "hairpin" hybrid of over 7 base pairs, allowing a loop of up to 4 base pairs Any sequence of 8 base pairs or more that has a perfect inverted repeat within a 50 bp interval such that an internal hairpin can be formed Following identification, the sequence is manually adjusted as follows. Third bases of codons will be changed to remove hairpins or decrease the number of paring bases in the hairpin to less than five contiguous bases.

Where possible, third base codons will be changed, leaving the amino acid sequence unchanged, in order to decrease the GC content of a region to less than 65% over 20 bases.

Where possible, third base changes will be made, keeping te amino acids sequence the same, in order to remove internal hybrids or decrease the number of matching bases to less than 7.

The resulting synthetic DNA sequence will still encode the same protein but the codon usage will be adjusted to remove sequence structures that might cause errors in assembly, might lower assembly efficiency or otherwise cause problems in the technical procedure of gene synthesis and assembly.

Subsequent parsing of the target sequence results in a set of shorter DNA sequences that overlap to cover the entire length of the target polynucleotide in overlapping sets.

Typically, a gene of 1000 bases pairs would be broken down into 20 100-mers where 10 of these comprise one strand and 10 of these comprise the other strand. They would be selected to overlap on each strand by 25 to 50 base pairs.

The degeneracy of the genetic code permits substantial freedom in the choice of codons for any particular amino acid sequence. Transgenic organisms such as plants frequently prefer particular codons that, though they encode the same protein, can differ from the codons in the organism from which the gene was derived. For example, U.S. Pat. No. 5,380,831 to Adang et al. describes the creation of insect resistant transgenic plants that express the Bacillus thuringiensis (Bt) toxin gene. The Bt crystal protein, an insect toxin, is encoded by a full-length gene that is poorly expressed in transgenic plants. In order to improve expression in plants, a synthetic gene encoding the protein containing codons preferred in plants was substituted for the natural sequence. The invention disclosed therein comprised a chemically synthesized gene encoding an insecticidal protein which is frequently equivalent to a native insecticidal protein of Bt. The synthetic gene was designed to be expressed in plants at a level higher than a native Bt gene.

In designing a target polynucleotide that encodes a particular polypeptide, the hydropathic index of amino acids can be considered. The importance of the hydropathic amino acid index in conferring interactive biologic function on a protein is generally understood in the art. Each amino acid has been assigned a hydropathic index on the basis of their hydrophobicity and charge characteristics, these are: Isoleucine (+4.5); valine (+4.2); leucine (+3.8); phenylalanine (+2.8); cysteine/cystine (+2.5); methionine (+1.9); alanine (+1.8); glycine (−0.4); threonine (47); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (45).

It is known in the art that certain amino acids can be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±I are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutarnate (+3.0±1); serine (+0.3); asparagine (+0.2); glutamine (+0.2); glycine (0); threonine (44); proline (−0.5±1); alanine (45); histidine −0.5); cysteine (−1.0); methionine (−1.3); valine 1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent polypeptide. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutarnate and aspartate; serine and threonine; glutamine and asparagine; and valine, leucine and isoleucine.

Aspects of the invention can be implemented in hardware or software, or a combination of both. However, preferably, the algorithms and processes of the invention are implemented in one or more computer programs executing on programmable computers each comprising at least one processor, at least one data storage system (including volatile and non-volatile memory and/or storage elements), at least one input device, and at least one output device. Program code is applied to input data to perform the functions described herein and generate output information. The output information is applied to one or more output devices, in known fashion.

Each program can be implemented in any desired computer language (including machine, assembly, high level procedural, or object oriented programming languages) to communicate with a computer system. In any case, the language can be a compiled or interpreted language.

Each such computer program is preferably stored on a storage medium or device (e.g., ROM, CD-ROM, tape, or magnetic diskette) readable by a general or special purpose programmable computer, for configuring and operating the computer when the storage media or device is read by the computer to perform the procedures described herein. The inventive system can also be considered to be implemented as a computer-readable storage medium, configured with a computer program, where the storage medium so configured causes a computer to operate in a specific and predefined manner to perform the functions described herein.

Thus, in another embodiment, the invention provides a computer program, stored on a computer-readable medium, for generating a target polynucleotide sequence. The computer program includes instructions for causing a computer system to: 1) identify an initiating polynucleotide sequence contained in the target polynucleotide sequence; 2) parse the target polynucleotide sequence into multiply distinct, partially complementary, oligonucleotides; and 3) control assembly of the target polynucleotide sequence by controlling the bi-directional extension of the initiating polynucleotide sequence by the sequential addition of partially complementary oligonucleotides resulting in a contiguous double-stranded polynucleotide. The computer program will contain an algorithm for parsing the sequence of the target polynucleotide by generating a set of oligonucleotides corresponding to a polypeptide sequence. The algorithm utilizes a polypeptide sequence to generate a DNA sequence using a specified codon table. The algorithm then generates a set of parsed oligonucleotides corresponding to the (+) and (−) strands of the DNA sequence in the following manner:

1. The DNA sequence GENE[], an array of bases, is generated from the protein sequence AA[], an array of amino acids, using a specified codon table. An example of the codon table for *E. coli* type II codons, is listed below.
   a. parameters
      i. N Length of protein in amino acid residues
      ii. L=3N Length of gene in DNA bases
      iii. Q Length of each component oligonucleotide
      iv. X=Q/2 Length of overlap between oligonucleotides
      v. W=3N/Q Number of oligonucleotides in the F set
      vi. Z=3N/Q+1 Number of oligonucleotides in the R set
      vii. F[1:W]set of (+) strand oligonucleotides
      viii. R[L:Z]set of (−) strand oligonucleotides
      ix. AA[1:N]array of amino acid residues
      x. GENE[1:L]array of bases comprising the gene
   b. Obtain or design a protein sequence AA[ ] consisting of a list of amino acid residues.
   c. Generate the DNA sequence, GENE [ ], from the protein sequence, AA[ ]
      i. For I=1 to N
      ii. Translate AA [J]from codon table generating GENE [I:1+2]
      iii. I=I+3
      iv. J=J+1
      v. Go to ii 2. Two sets of overlapping oligonucleotides are generated from GENE[]; F[] covers the (+) strand and R[] is a complementary, partially overlapping set covering the (−) strand.
   a. Generate the F[ ] set of oligos
      i. For I=1 to W
      ii. F[I]=GENE [I:I+Q−1]
      iii. I=I+Q
      iv. Go to ii b. Generate the R set of oligos
   i. J=W
   ii. For I=1 to W
   iii. R[I]=GENE [W:W-Q]
   iv. J=J-Q
   v. Go to iii
c. Result is two set of oligos F[ ] and R[ ] of Q length
d. Generate the final two finishing oligos
   i. S[1]=GENE [Q/2:1]
   ii. S[2]=GENE [L-Q/2:L]

Subsequently, if desired, oligonucleotide set assembly can be established by the following algorithm:

Two sets of oligonucleotides F[1:W] R[1:Z] S[1:2]

3. Step 1
   a. For I=1 to W
   b. Anneal F[I], F[I+1], R[I]; place in T[I]
   c. Anneal F[I+2], R[I+1], R[I+2]T[I+1]
   d. I=I+3
   e. Go to b
4. Step 2
   a. Do the following until only a single reaction remains
      i. For I=1 to W/3
      ii. Ligate T[I], T[I+1]
      iii. I=I+2
      iv. Go to ii

| CODON TABLE (*E. coli* Class II preferred usage) | |
|---|---|
| PHE | TTC |
| SER | TCT |
| TYR | TAC |
| CYS | TGG |
| TER | TGA |
| TRP | TGG |
| ILE | ATC |
| MET | ATG |
| THR | ACC |
| LEU | CTG |
| PRO | CCG |
| HIS | CAC |
| GLN | CAG |
| ARG | CGT |
| VAL | GTT |
| ALA | GCG |
| ASN | AAC |
| LYS | AAA |
| ASP | GAC |
| GLU | GAA |
| GLY | GGT |

Algorithms of the invention useful for assembly of a target polynucleotide can further be described as Perl script as set forth below. ALGORITHM 1 provides a method for converting a protein sequence into a polynucleotide sequence using *E. Coli* codons:

```
#$sequence is the protein sequence in single letter amino acid code
#$seglen is the length of the protein sequence
#$amino acid is the individual amino acid in the sequence
#$codon is the individual DNA triplet codon in the Gene sequence
#$DNAsquence is the gene sequence in DNA bases
#$baselen is the length of the DNA sequence in bases
#$seglen=length($sequence)
$baselen=$seglen * 3;
for ($n=0;$n<=$seglen; $n++)
{aminoacid=substr($sequence, $n,1);
```

The following list provides the class II codon preference in Perl for *E. coli*

```
if ($aminoacid eq "m") {$codon = "ATG";}
    elsif ($aminoacid eq "f")   {$codon = "TTC";}
    elsif ($aminoacid eq "l")   {$codon = "CTG";}
    elsif ($aminoacid eq "s")   {$codon = "TCT";}
    elsif ($aminoacid eq "y")   {$codon = "TAC";}
    elsif ($aminoacid eq "c")   {$codon = "TGC";}
    elsif ($aminoacid eq "w")   {$codon = "TGG";}
    elsif ($aminoacid eq "i")   {$codon = "ATC";}
    elsif ($aminoacid eq "t")   {$codon = "ACC";}
    elsif ($aminoacid eq "p")   {$codon = "CCG";}
    elsif ($aminoacid eq "q")   {$codon = "CAG";}
    elsif ($aminoacid eq "r")   {$codon = "CGT";}
    elsif ($aminoacid eq "v")   {$codon = "GTT";}
    elsif ($aminoacid eq "a")   {$codon = "GCG";}
    elsif ($aminoacid eq "n")   {$codon = "AAC";}
    elsif ($aminoacid eq "k")   {$codon = "AAA";}
    elsif ($aminoacid eq "d")   {$codon = "GAC";}
    elsif ($aminoacid eq "e")   {$codon = "GAA";}
    elsif ($aminoacid eq "g")   {$codon = "GGT";}
    elsif ($aminoacid eq "h")   {$codon = "CAC";}
    else {$codon = " "};
$DNAsequence = $DNAsequence + $codon;
```

ALGORITHM 2 provides a method for parsing a polynucleotide sequence into component forward and reverse oligonucleotides that can be reassembled into a complete target polynucleotide encoding a target polypeptide:

```
#$oligoname is the identifier name for the list and for each component #oligonucleotide
#$OL is the length of each component oligonucleotide
#$Overlap is the length of the overlap in bases between each forward and each #reverse oligonucleotide
#$sequence is the DNA sequence in bases
#$seqlen is the length of the DNA sequence in bases
#$bas is the individual base in a sequence
#$forseq is the sequence of a forward oligonucleotide
#$revseq is the sequence of a reverse oligonucleotide
#$revcomp is the reverse complemented sequence of the gene
#$oligonameF- [ ] is the list of parsed forward oligos
#$oligonameR- [ ] is the list of parsed reverse oligos
$Overlap = <STDIN>;
$seqlen = length ($sequence);
#convert forward sequence to upper case if lower case
$forseq = " ";
for ($j = 0; $j <= seqlen-1; $j + +)
{    ($bas = substr ($sequence,$j,1);
    if ($bas eq "a") {$cfor = "A";}
        elsif ($bas eq "t")   {$cfor = "T";}
        elsif ($bas eq "c")   {$cfor = "C";}
        elsif ($bas eq "g")   {$cfor = "G";}
        elsif ($bas eq "A")   {$cfor = "A";}
        elsif ($bas eq "T")   {$cfor = "T";}
        elsif ($bas eq "C")   {$cfor = "C";}
        elsif ($bas eq "G")   {$cfor = "G";}
        else {$cfor = "X"};
    $forseq = $forseq.$cfor;
    print OUT "$j \n";
}
```

The reverse complement of the sequence generated above is identified by:

```
$revcomp = " ";
for ($i = $seqlen-1; $i >= 0); $i- -)
}   $base = substr($sequence,$i,1);
    if ($base eq "a") {$comp = "T";}
        elsif ($base eq "t")   {$comp = "A";}
        elsif ($base eq "g")   {$comp = "C";}
        elsif ($base eq "c")   {$comp = "G";}
        elsif ($base eq "A")   {$comp = "T";}
```

-continued

```
    elsif ($base eq "T")    {$comp = "A";}
    elsif ($base eq "G")    {$comp = "C";}
    elsif ($base eq "C")    {$comp = "G";}
    else {$comp = "X"};
    $revcomp = $revcomp.$comp;
}
#now do the parsing
#generate the forward oligo list
print OUT "Forward oligos\n";
print "Forward oligos\n";
$r = 1;
for ($i = 0; $i <= $seqlen -1; $i+=$OL)
{    $oligo = substr($sequence,$i,$OL);
     print OUT "$oligname F- $r      $oligo\n";
     print "$oligname F- $r     $oligo\n";
     $r = $r + 1;
}
#generate the forward reverse list
$r = 1;
for ($i = $seqlen - $Overlap - $OL; $i >= 0; $i-=$OL)
{
    print OUT "\n";
    print "\n";
    $oligo = substr($revcomp,$i,$OL);
    print OUT "$oligname R- $r      $oligo\n";
    print "$oligname R- $r-     $oligo\n";
    $r = $r + 1;
}
#Rectify and print out the last reverse oligo consisting of 1/2 from
the beginning # of the reverse complement.
$oligo = substr($revcomp,1,$Overlap);
print OUT "$oligo";
print "$oligo";
```

The invention further provides a computer-assisted method for synthesizing a target polynucleotide encoding a target polypeptide derived from a model sequence using a programmed computer including a processor, an input device, and an output device, by inputting into the programmed computer, through the input device, data including at least a portion of the target polynucleotide sequence encoding a target polypeptide. Subsequently, the sequence of at least one initiating polynucleotide present in the target polynucleotide sequence is determined and a model for synthesizing the target polynucleotide sequence is derived. The model is based on the position of the initiating sequence in the target polynucleotide sequence using overall sequence parameters necessary for expression of the target polypeptide in a biological system. The information is outputted to an output device which provides the means for synthesizing and assembling to target polynucleotide.

Figure 4:
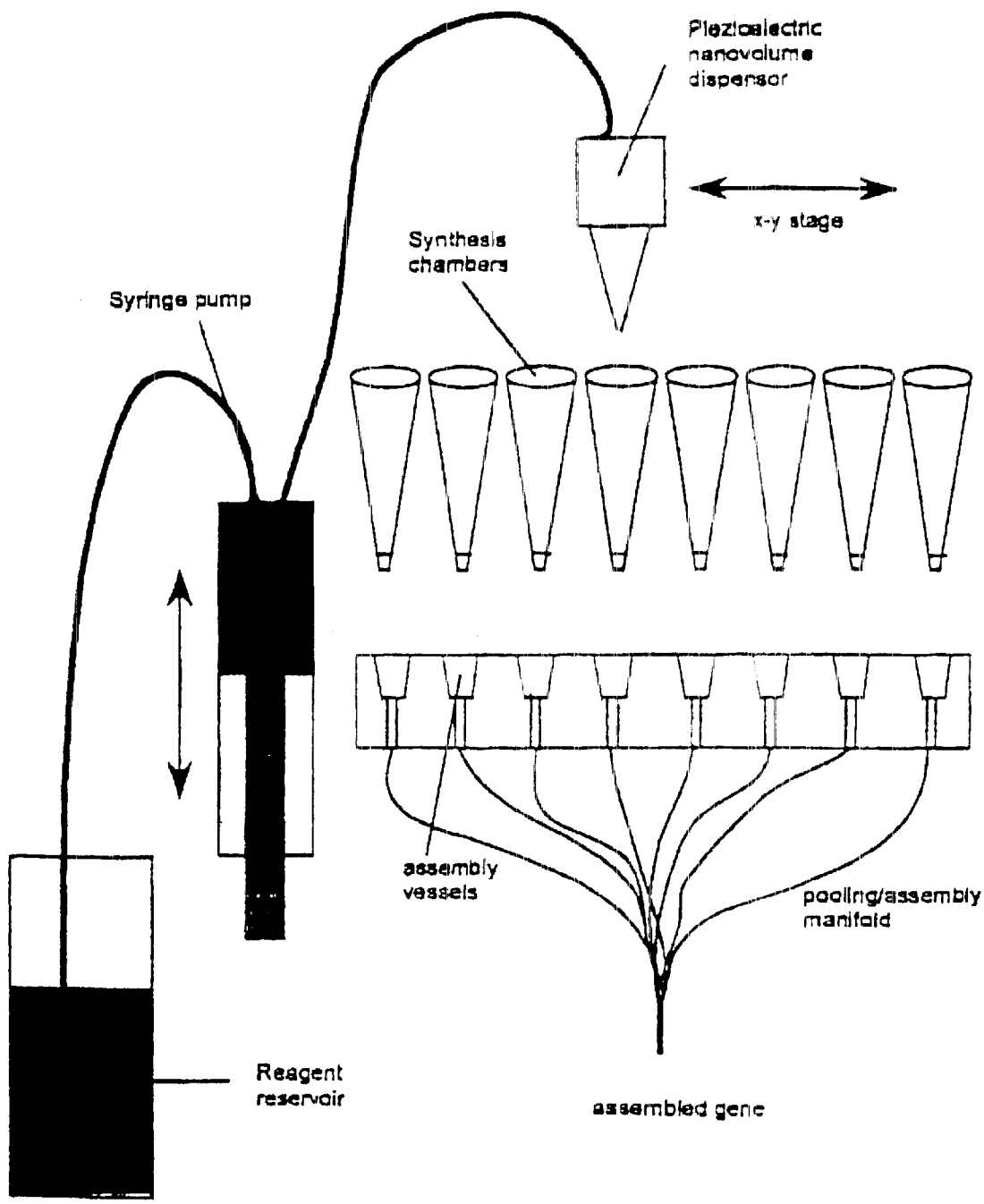
FIG. 4 depicts a schematic of the polynuceotide synthesis modules. A nanodispensing head with a plurality of valves will deposit synthesis chemicals in assembly vessels. Chemical distribution from the reagent reservoir can be controlled using a syringe pump. Underlying the reaction chambers is a set of assembly vessels linked to microchannels that will move fluids by microfluidics.

It is understood that any apparatus suitable for polynucleotide synthesis can be used in the present invention. Various non-limiting examples of apparatus, components, assemblies and methods are described below. For example, in one embodiment, it is contemplated that a nanodispensing head with up to 16 valves can be used to deposit synthesis chemicals in assembly vessels (FIG. 4). Chemicals can be controlled using a syringe pump from the reagent reservoir. Because of the speed and capability of the ink-jet dispensing system, synthesis can be made very small and very rapid. Underlying the reaction chambers is a set of assembly vessels linked to microchannels that will move fluids by microfluidics. The configuration of the channels will pool pairs and triplexes of oligonucleotides systematically using, for example, a robotic device. However, pooling can be accomplished using fluidics and without moving parts.

Figure 5:
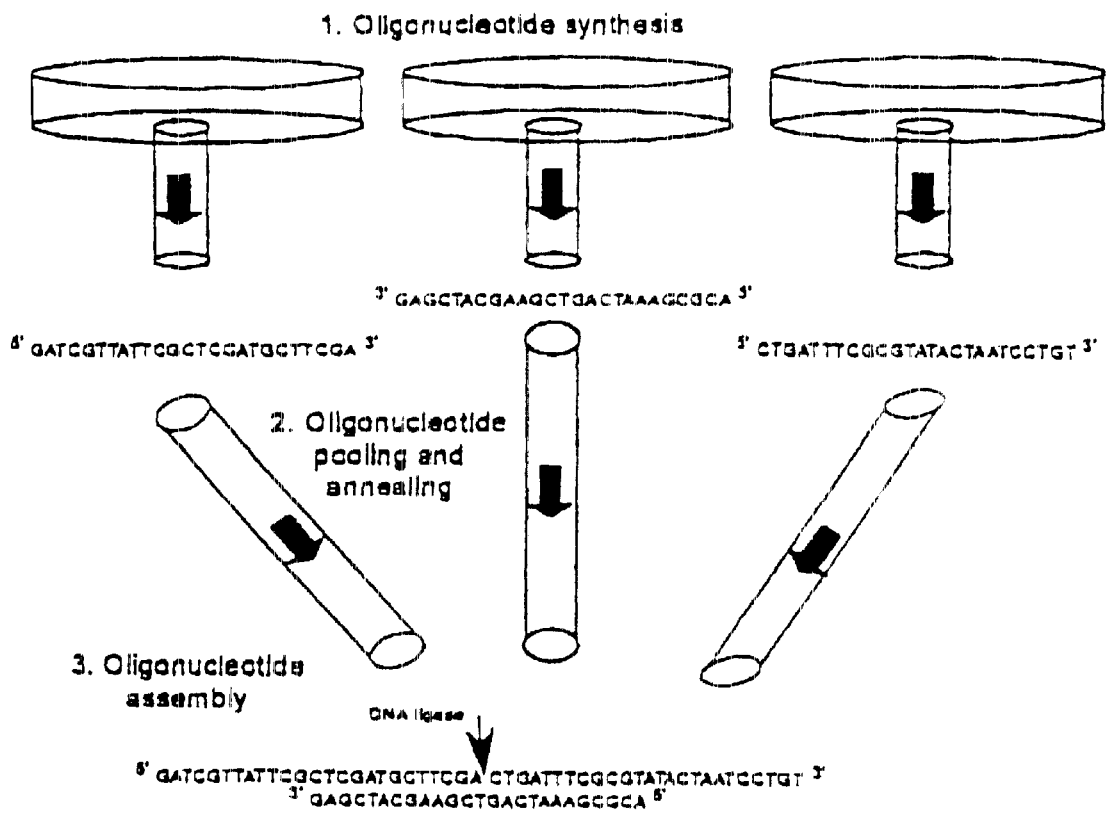
FIG. 5 depicts that oligonucleotide synthesis, oligonucleotide assembly by pooling and annealing, and ligation can be accomplished using microfluidic mixing.

As shown in FIG. 5, oligonucleotide synthesis, oligonucleotide assembly by pooling and annealing, and ligation can be done using microfluidic mixing, resulting in the same set of critical triplex intermediates that serves as the substrate for annealing, ligation and oligonucleotide joining. DNA ligase and other components can be placed in the buffer fluid moving through the instrument microchambers. Thus, synthesis and assembly can be carried out in a highly controlled way in the same instrument.

Figure 6:
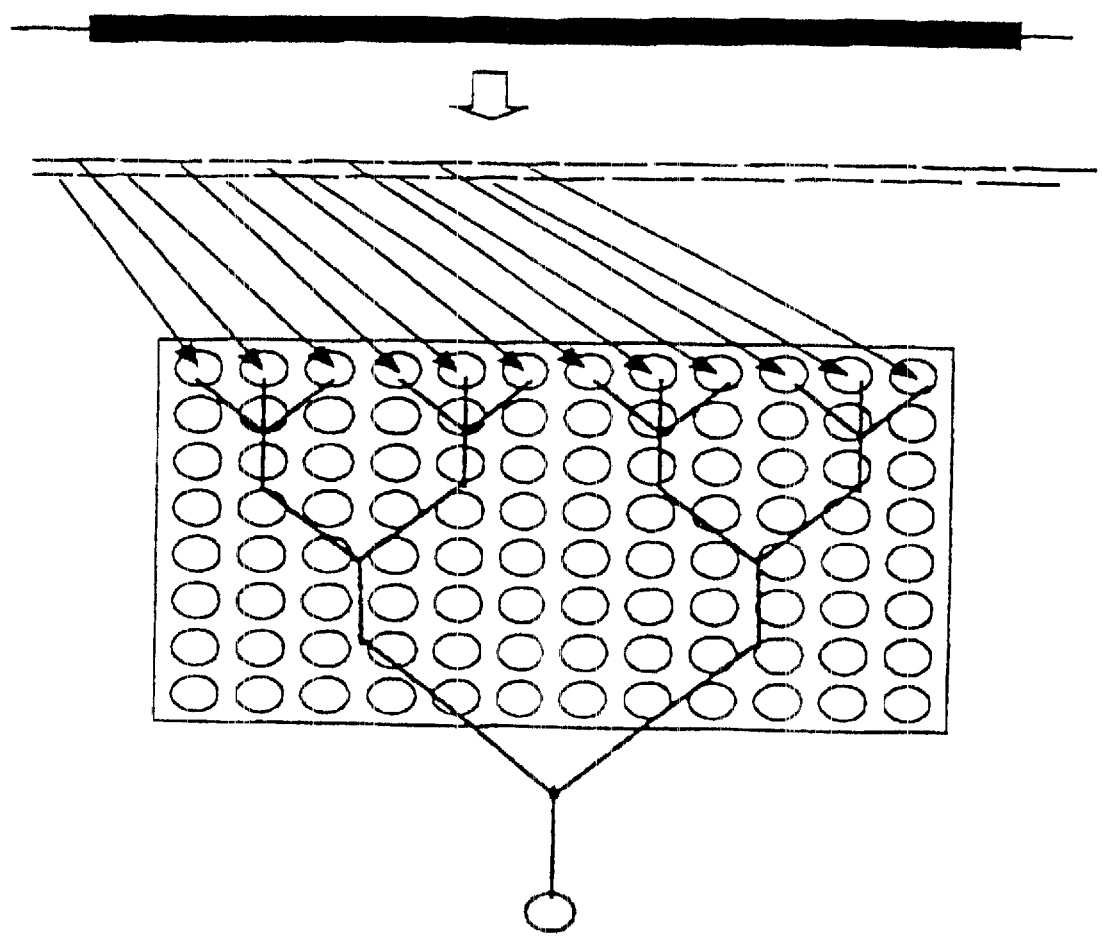
FIG. 6 depicts the sequential pooling of oligonucleotides synthesized in arrays.
Figure 7:
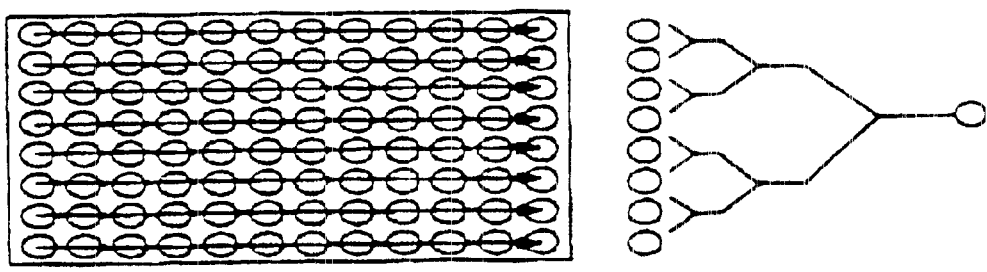
FIG. 7 depicts the pooling stage of the oligonucleotide components through the manifold assemblies resulting in the complete assembly of all oligonucleotides from the array.
Figure 8:
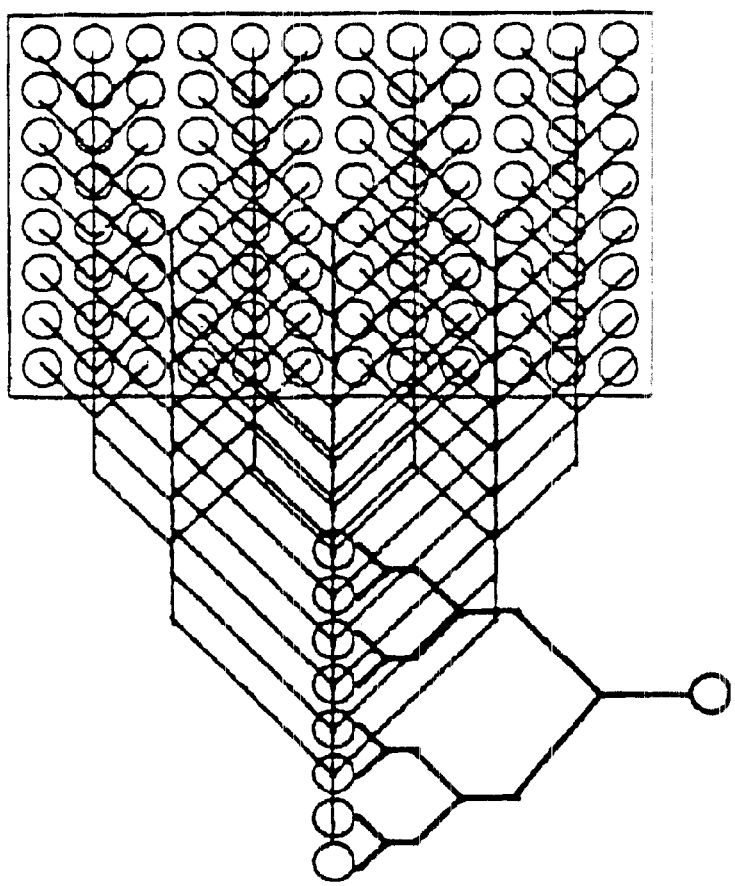
FIG. 8 depicts an example of an assembly module comprising a complete set of pooling manifolds produced using microfabrication in a single unit. Various configurations of the pooling manifold will allow assembly of increased numbers of well arrays of parsed component oligonucleotides.

As shown in FIG. 6, the pooling manifold can be produced from non-porous plastic and designed to control sequential pooling of oligonucleotides synthesized in arrays. Oligonucleotide parsing designed from a gene sequence designed in the computer can be programmed for synthesis where (+) and (−) strands are placed in alternating wells of the array. Following synthesis in this format, the 12 row sequences of the gene are directed into the pooling manifold that systematically pools three wells into reaction vessels forming the critical triplex structure. Following temperature cycling for annealing and ligation, four sets of triplexes are pooled into 2 sets of 6 oligonucleotide products, then 1 set of 12 oligonucleotide products. Each row of the synthetic array is associated with a similar manifold resulting in the first stage of assembly of 8 sets of assembled oligonucleotides representing 12 oligonucleotides each. As shown in FIG. 7, the second manifold pooling stage is controlled by a single manifold that pools the 8 row assemblies into a single complete assembly. Passage of the oligonucleotide components through the two manifold assemblies (the first 8 and the second single) results in the complete assembly of all 96 oligonucleotides from the array. The assembly module (FIG. 8) of Genewriter™ can include a complete set of 7 pooling manifolds produced using microfabrication in a single plastic block that sits below the synthesis vessels. Various configurations of the pooling manifold will allow assembly of 96,384 or 1536 well arrays of parsed component oligonucleotides.

Figure 9:
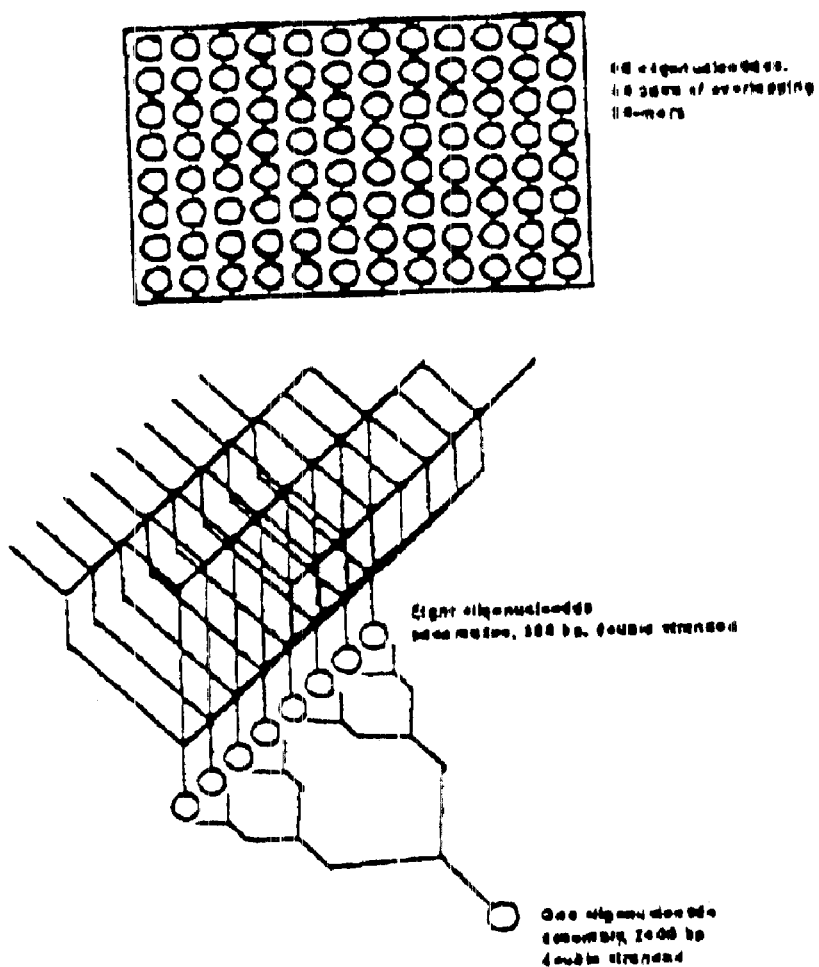
FIG. 9 depicts the configuration for the assembly of oligonucleotides synthesized in a pre-defined array. Passage through the assembly device in the presence of DNA ligase and other appropriate buffer and chemical components will facilitate double stranded polynucleotide assembly.
Figure 10:
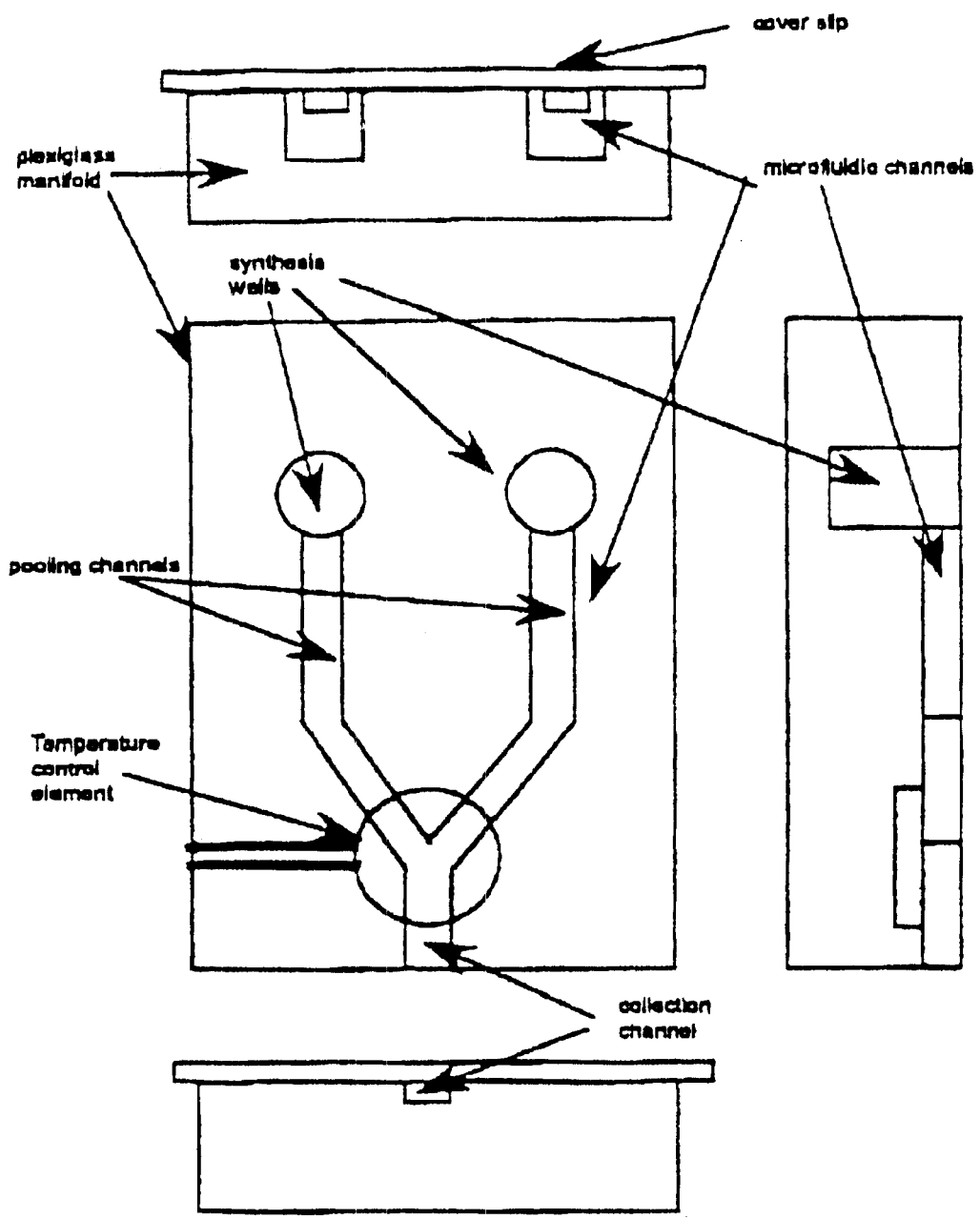
FIG. 10 depicts an example of the pooling device design. Microgrooves or microfluidic channels are etched into the surface of the pooling device. The device provides a microreaction vessel at the junction of two channels for 1) mixing of the two streams, 2) controlled temperature maintenance or cycling a the site of the junction and 3) expulsion of the ligated mixture from the exit channel into the next set of pooling and ligation chambers.

The initial configuration is designed for the assembly of 96 oligonucleotides synthesized in a pre-defined array, composed of 48 pairs of overlapping 50 mers. Passage through the assembly device in the presence of DNA ligase and other appropriate buffer and chemical components, and with appropriate temperature controls on the device, will assembly these into a single 2400 base double stranded gene assembly (FIG. 9). The basic pooling device design can be made of Plexiglas™ or other type of co-polymer with microgrooves or microfluidic channels etched into the surface and with a temperature control element such as a Peltier circuit underlying the junction of the channels. This results in a microreaction vessel at the junction of two channels for 1) mixing of the two streams, 2) controlled temperature maintenance or cycling a the site of the junction and 3) expulsion of the ligated mixture from the exit channel into the next set of pooling and ligation chambers.

Figure 11:
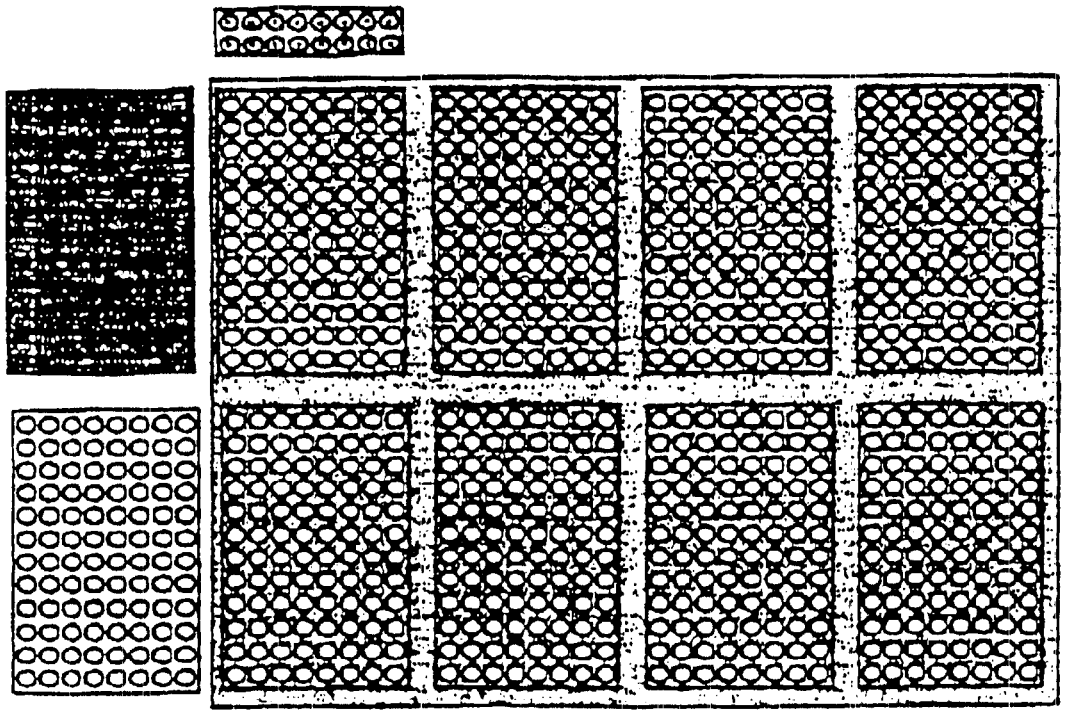
FIG. 11 depicts the design of a polynucleotide synthesis platform comprising microwell plates addressed with a plurality of channels for microdispensing.
Figure 12:
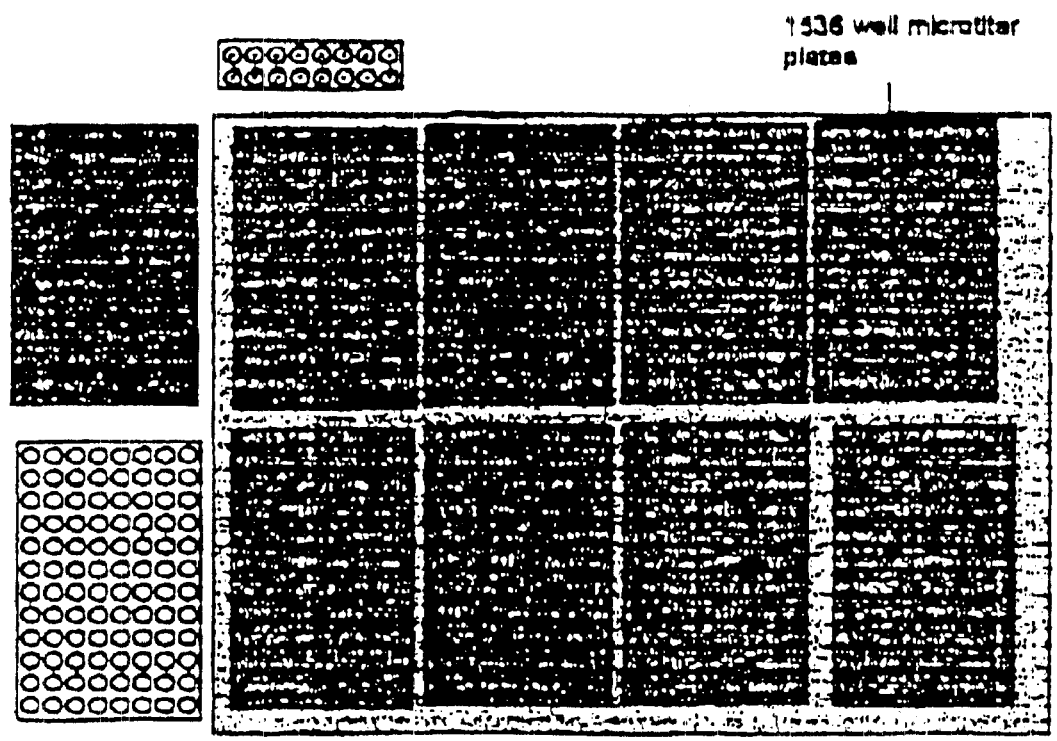
FIG. 12 depicts an example of a high capacity polynucleotide synthesis platform using high density microwell microplates capable of synthesizing in excess of 1536 component oligonucleotides per plate.

As shown in FIG. 11, the assembly platform design can consist of 8 synthesis microwell plates in a 96 well configuration, addressed with 16 channels of microdispensing. Below each plate is: 1) an evacuation manifold for removing synthesis components; and 2) an assembly manifold based on the schematic in FIG. 9 for assembling component oligonucleotides from each 96-well array. FIG. 12 shows a higher capacity assembly format using 1536-well microplates and capable of synthesis of 1536 component oligonucleotides per plate. Below each plate is: 1) an evacuation manifold for removing synthesis components; and 2) an assembly manifold assembly for assembling 1536 component oligonucleotides from each 1536-well array. Pooling and assembly strategies can be based on the concepts used for 96-well plates.

Figure 13:
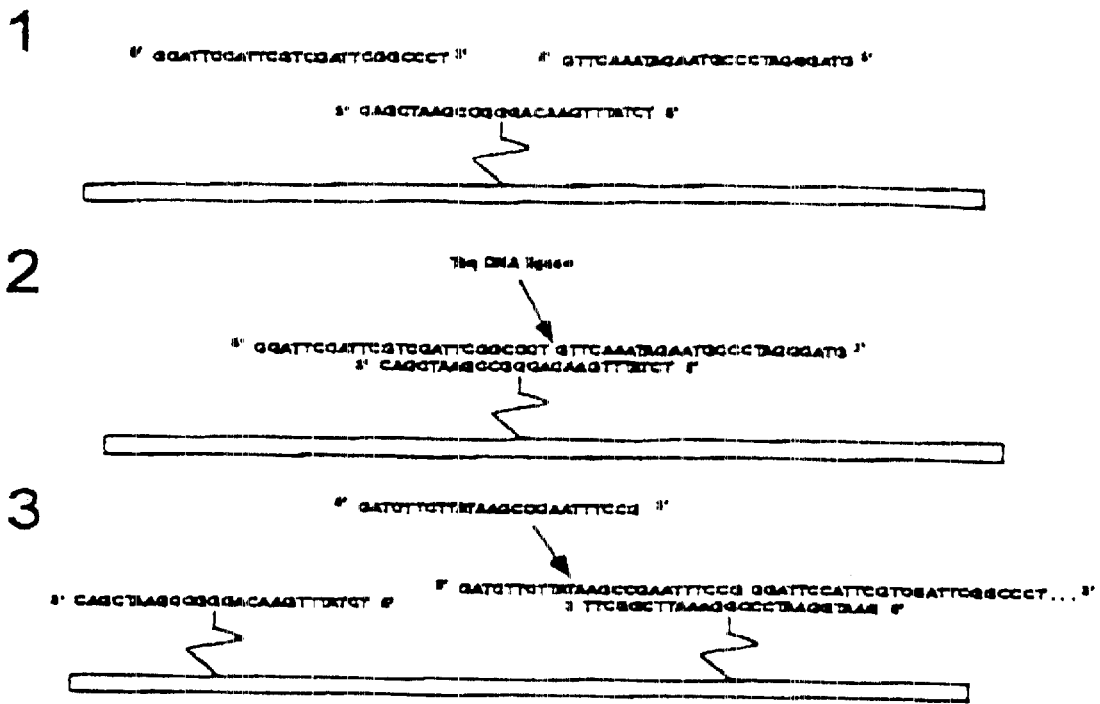
FIG. 13 depicts a polynucleotide assembly format using surface-bound oligonucleotide synthesis rather than soluble synthesis. In this configuration, oligonucleotides are synthesized with a linker that allows attachment to a solid support.
Figure 14:
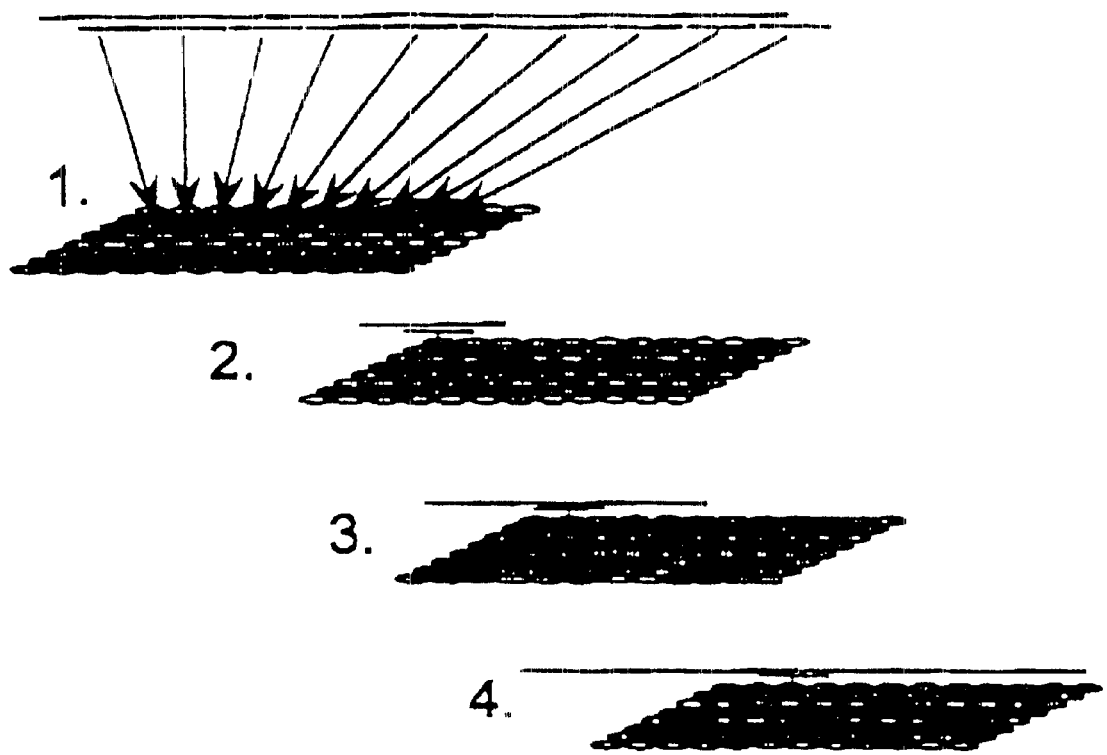
FIG. 14 depicts a diagram of systematic polynucleotide assembly on a solid support. A set of parsed component oligonucleotides are arranged in an array with a stabilizer oligonucletoide attached. A set of ligation substrate oligonucleotides are placed in the solution and systematic assembly is carried out in the solid phase by sequential annealing, ligation and melting.

An alternative assembly format includes using surface-bound oligonucleotide synthesis rather than soluble synthesis on CPG glass beads (FIG. 13). In this configuration, oligonucleotides are synthesized with a hydrocarbon linker that allows attachment to a solid support. Following parsing of component sequences and synthesis, the synthesized oligonucleotides are covalently attached to a solid support such that the stabilizer is attached and the two ligation substrates added to the overlying solution. Ligation occurs as mediated by DNA ligase in the solution and increasing temperature above the Tm removes the linked oligonucleotides by thermal melting. As shown in FIG. 14 the systematic assembly on a solid support of a set of parsed component oligonucleotides can be arranged in an array with the set of stabilizer oligonucletoide attached. The set of ligation substrate oligonucleotides are placed in the solution and, systematic assembly is carried out in the solid phase by sequential annealing, ligation and melting which moves the growing DNA molecules across the membrane surface.

Figure 15:
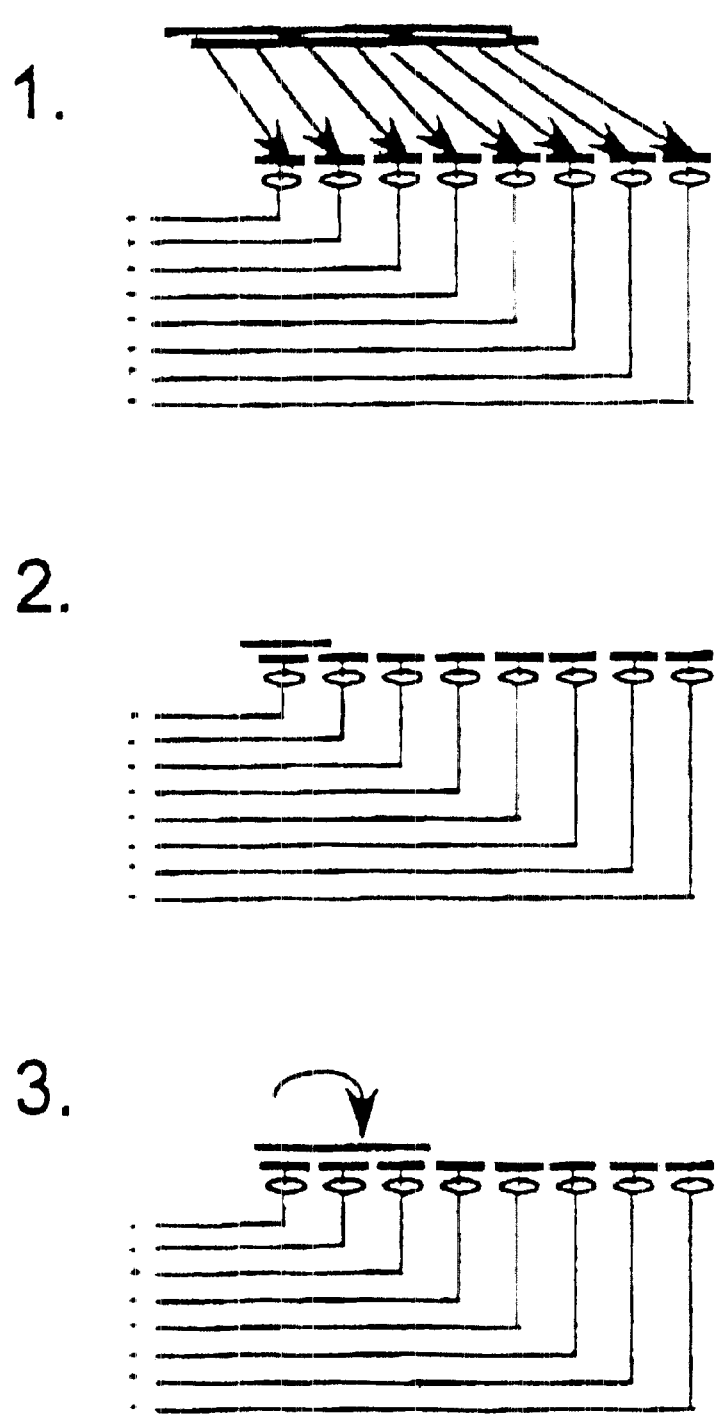
FIG. 15 depicts polynucleotide assembly using component oligonucleotides bound to a set of metal electrodes on a microelectronic chip. Each electrode can be controlled independently with respect to current and voltage.
Figure 16:
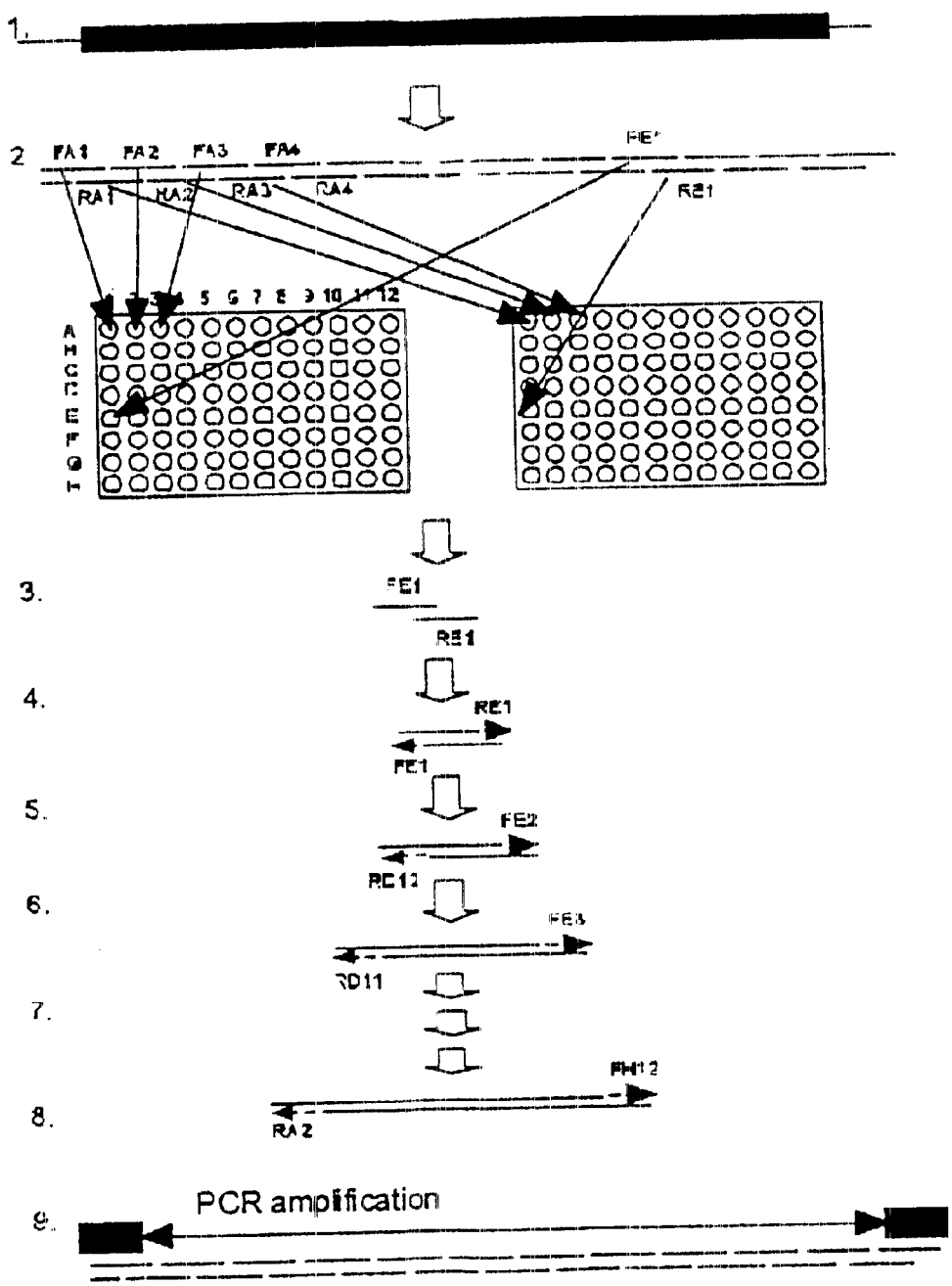
FIG. 16 depicts generally a primer extension assembly method of the invention.
Figure 17:
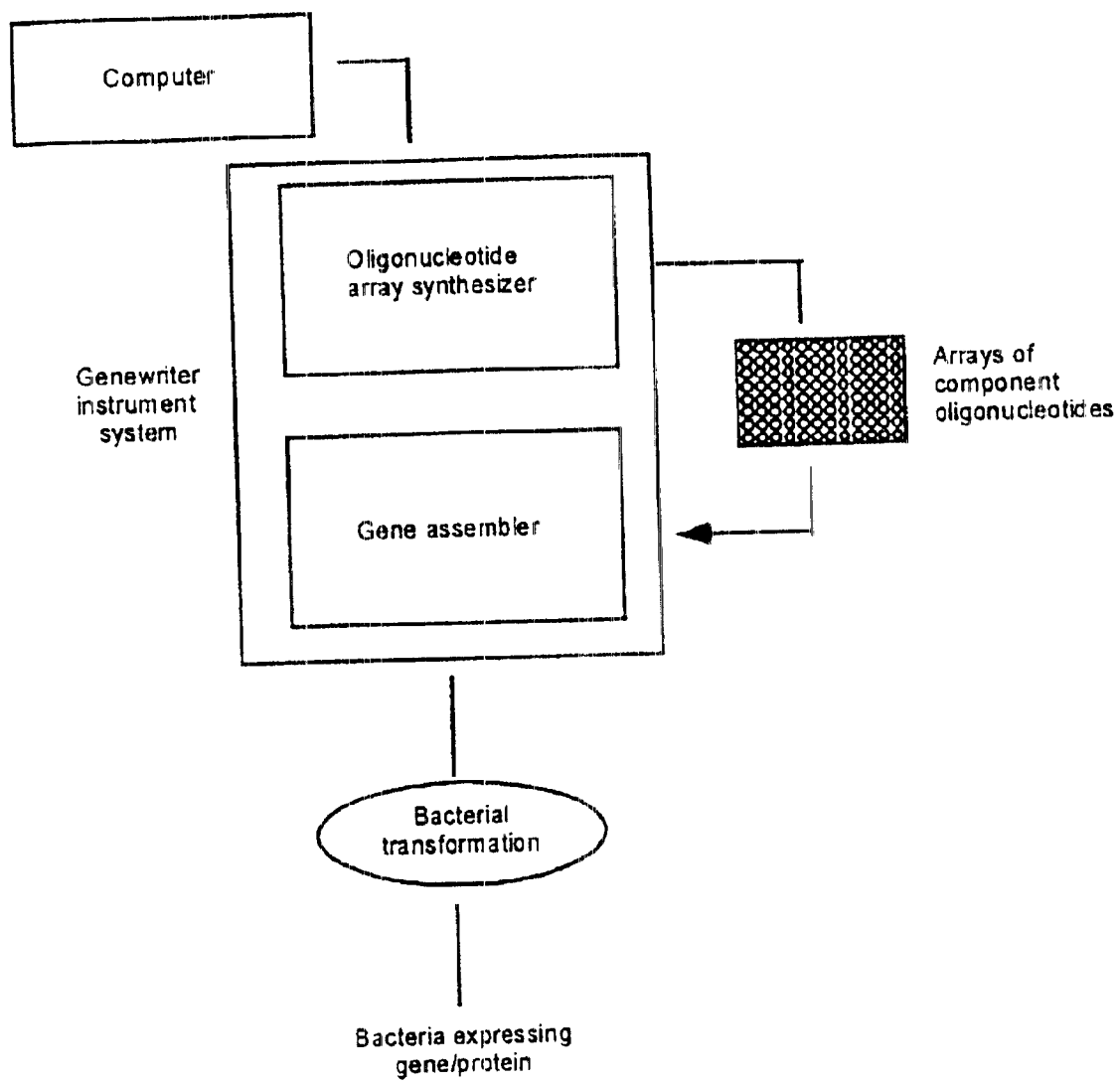
FIG. 17 provides a system diagram of the invention.
Figure 18:
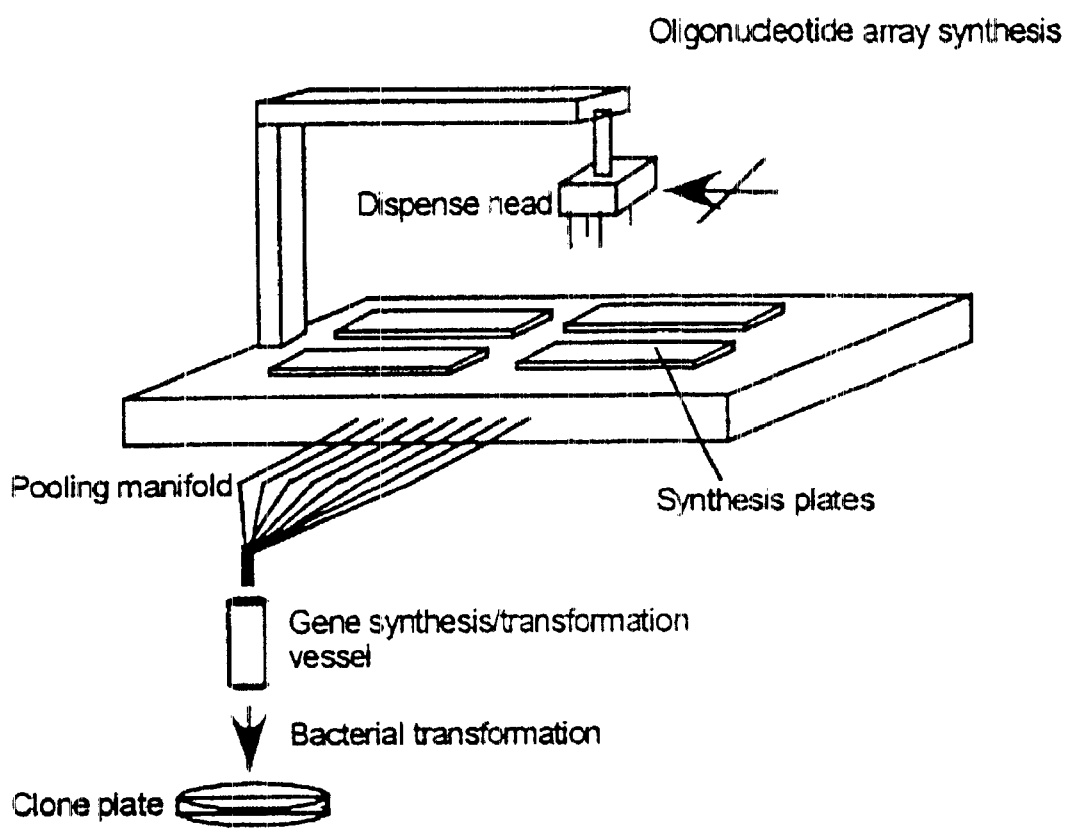
FIG. 18 depicts a perspective view of an instrument of the invention.
Figure 19:
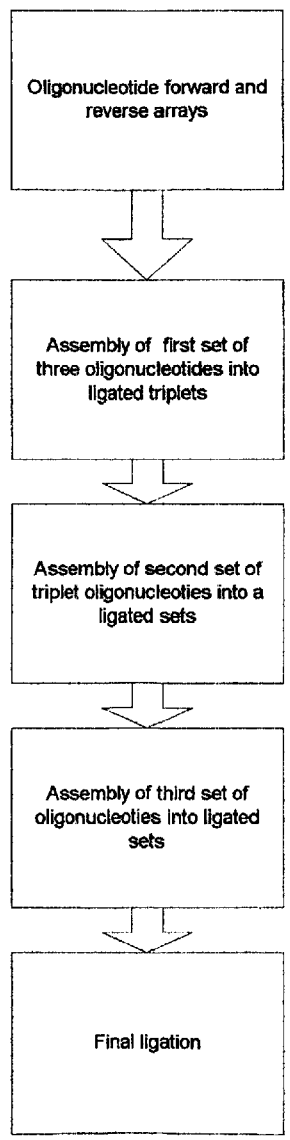
FIG. 19 depicts two flow-charts showing the generation of self-assembling oligonucleotide arrays

FIG. 15 shows an additional alternative means for oligonucleotide assembly, by binding the component oligonucleotides to a set of metal electrodes on a microelectronic chip, where each electrode can be controlled independently with respect to current and voltage. The array contains the set of minus strand oligonucleotides. Placing a positive change on the electrode will move by electrophoresis the component ligase substrate oligonucleotide onto the surface where annealing takes place. The presence of DNA ligase mediates covalent joining or ligation of the components. The electrode is then turned off or a negative charge is applied and the DNA molecule expulsed from the electrode. The next array element containing the next stabilizer oligonucleotide from the parsed set is turned on with a positive charge and a second annealing, joining and ligation with the next oligonucleotide in the set carried out. Systematic and repetitive application of voltage control, annealing, ligation and denaturation will result in the movement of the growing chain across the surface as well as assembly of the components into a complete DNA molecule.

The invention further provides methods for the automated synthesis of target polynucleotides. For example, a desired sequence can be ordered by any means of communication available to a user wishing to order such a sequence. A "user", as used herein, is any entity capable of communicating a desired polynucleotide sequence to a server. The sequence may be transmitted by any means of communication available to the user and receivable by a server. The user can be provided with a unique designation such that the user can obtain information regarding the synthesis of the polynucleotide during synthesis. Once obtained, the transmitted target polynucleotide sequence can be synthesized by any method set forth in the present invention.

The invention further provides a method for automated synthesis of a polynucleotide, by providing a user with a mechanism for communicating a model polynucleotide sequence and optionally providing the user with an opportunity to communicate at least one desired modification to the model sequence. The invention envisions a user providing a model sequence and a desired modification to that sequence which results in the alteration of the model sequence. Any modification that alters the expression, function or activity of a target polynucleotide or encoded target polypeptide can be communicated by the user such that a modified polynucleotide or polypeptide is synthesized or expressed according to a method of the invention. For example, a model polynucleotide encoding a polypeptide normally expressed in a eukaryotic system can be altered such that the codons of the resulting target polynucleotide are conducive for expression of the polypeptide in a prokaryotic system. In addition, the user can indicate a desired modified activity of a polypeptide encoded by a model polynucleotide. Once provided, the algorithms and methods of the present invention can be used to synthesize a target polynucleotide encoding a target polypeptide believed to have the desired modified activity. The methods of the invention can be further utilized to express the target polypeptide and to screen for the desired activity. It is understood that the methods of the invention provide a means for synthetic evolution whereby any parameter of polynucleotide expression and/or polypeptide activity can be altered as desired.

Once the transmitted model sequence and desired modification are provided by the user, the data including at least a portion of the model polynucleotide sequence is inputted into a programmed computer, through an input device. Once inputted, the algorithms of the invention are used to determine the sequence of the model polynucleotide sequence containing the desired modification and resulting in a target polynucleotide containing the modification. Subsequently, the processor and algorithms of the invention is used to identify at least one initiating polynucleotide sequence present in the polynucleotide sequence. A target polynucleotide (i.e., a modified model polynucleotide) is identified and synthesized.

EXAMPLES

Nucleic Acid Synthesis Design Protocol

For the purposes of assembling a synthetic nucleic acid sequence encoding a target polypeptide, a model polypeptide sequence or nucleic acid sequence is obtained and analyzed using a suitable DNA analysis package, such as, for example, MacVector or DNA Star. If the target protein will be expressed in a bacterial system, for example, the model sequence can be converted to a sequence encoding a polypeptide utilizing *E. coli* preferred codons (i.e., Type I, Type II or Type II codon preference). The present invention provides the conversion programs Codon I, Codon II or Codon III. However, a nucleic acid sequence of the invention can be designed to accommodate any codon preference of any prokaryotic or eukaryotic organism.

In addition to the above codon preferences, specific promoter, enhancer, replication or drug resistance sequences can be included in a synthetic nucleic acid sequence of the invention. The length of the construction can be adjusted by padding to give a round number of bases based on about 25 to 100 bp synthesis. The synthesis of sequences of about 25 to 100 bp in length can be manufactured and assembled using the array synthesizer system and may be used without further purification. For example, two 96-well plates containing 100-mers could give a 9600 bp construction of a target sequence.

Subsequent to the design of the oligonucleotides needed for assembly of the target sequence, the oligonucleotides are parsed using ParseOligo™, a proprietary computer program that optimizes nucleic acid sequence assembly. Optional steps in sequence assembly include identifying and eliminating sequences that may give rise to hairpins, repeats or other difficult sequences. The parsed oligonucleotide list is transferred to the Synthesizer driver software. The individual oligonucleotides are pasted into the wells and oligonucleotide synthesis is accomplished.

The ParseOligo program reads a DNA sequence from a file and parses it into two sets of oligonucleotides, one set forward and one reverse, for synthetic gene assembly.

---

The input file format is as follows:

```
#Should be all text file
#Sequence name on the first line followed by paragraph mark
#The entire DNA sequences should be next without spaces or paragraph
#marks.

#The DNA sequence can be upper or lower case and lower case will be
#       converted.

#Any base other than G,A,T or C will be converted to X.

```

-continued

The input file format is as follows:

```

print "       P A R S E   O L I G O S    N\n";
print "               1 9 9 9        \n";
print "\n";
print "\n";
print "       Parse - A program for parsing a DNA sequence\n";
print "    into component oligonucleotides for synthetic gene assembly. \n";
print "\n";
print "\n";
print "         written by Glen A. Evans copyright c 1999.\n";
print "\n";
print "\n";
print "\n";
print "Enter name of the input DNA sequence file: ";
$a = <STDIN>;
chomp $a;
print "\n";
print "\n";
print "Enter the name of the output DNA oligonucleotide file: ";
$b = <STDIN>;
chomp $b;
print "\n";
print "\n";
open (IN, $a) || die "cannot open $a for reading: $!";
open (OUT,">$b") || die "cannot create $b: $!";
print "\n";
print "\n";
print "Enter the name for the oligo lists: ";
$oligname = <STDIN>;
chomp $oligname;
print "\n";
print "\n";
print "Enter the length of oligonucleotides: ";
$OL = <STDIN>;
chomp $OL;
print "\n";
print "\n";
print "Enter the required overlap: ";
$Overlap = <STDIN>;
chomp $Overlap;
#This is heart of the program - The rest is I/O.
$sequence = " ";
while (<IN>)
      {$sequence = <IN>;
}
chomp $sequence;
print OUT "The input DNA sequence is: \n";
print OUT "\n";
print OUT "$sequence";
print OUT "\n";
print OUT "\n";
print "The input DNA sequence is: \n";
print "\n";
print "$sequence";
print "\n";
print "\n";
$seqlen = length($sequence);
print OUT "The sequence is $seqlen bases long \n";
print OUT "\n";
print OUT "\n";
print "The sequence is $seqlen bases long \n";
print "\n";
print "\n";
#convert forward sequence to upper case if lower case
print OUT "The forward sequence converted to upper case \n";
print OUT "\n";
print OUT "\n";
print "The forward sequence converted to upper case \n";
print "\n";
print "\n";
$forseq = " ";
for ($j = 0; $j <= seqlen-1; $j + +)
{    $bas = substr($sequence,$j,1);
     if ($bas eq "a") {$cfor = "A";}
         elsif ($bas eq "t") {$cfor = "T";}
         elsif ($bas eq "c") {$cfor = "C";}
         elsif ($bas eq "g") {$cfor = "G";}
         elsif ($bas eq "A") {$cfor = "A";}
         elsif ($bas eq "T") {$cfor = "T";}
         elsif ($bas eq "C") {$cfor = "C";}
         elsif ($bas eq "G") {$cfor = "G";}
         else {$cfor = "X"};
     $forseq = $forseq.$cfor;
     print OUT "$j \n";
}
print OUT "$forseq";
print OUT "\n";
print OUT "\n";
print "$forseq";
print "\n";
print "\n";
#reverse complement the sequence
print OUT "The reverse complement of the DNA sequence:\n";
print OUT "\n";
print OUT "\n";
print "The reverse complement of the DNA sequence:\n";
print "\n";
print "\n";
$revcomp = " ";
for ($i = $seqlen-1; $i >= 0; $i- -)
{    $base = substr($sequence,$i,1);
     if ($base eq "a") {$comp = "T";}
         elsif ($base eq "t") {$comp = "A";}
         elsif ($base eq "g") {$comp = "C";}
         elsif ($base eq "c") {$comp = "G";}
         elsif ($base eq "A") {$comp = "T";}
         elsif ($base eq "T") {$comp = "A";}
         elsif ($base eq "G") {$comp = "C";}
         elsif ($base eq "C") {$comp = "G":}
         else {$comp = "X"};
     $revcomp = $revcomp.$comp;
}
print OUT "$revcomp\n";
print OUT "\n";
print "$revcomp\n";
print "\n";
#now do the parsing
#generate the oligo list
print OUT "Forward oligos\n";
print "Forward oligos\n";
$r = 1;
for ($i = 0; $i <= $seqlen -1; $i+=$OL)
{    $oligo = substr($sequence,$i,$OL);
     print OUT "$oligname F- $r        $oligo\n";
     print "$oligname F- $r        $oligo\n";
     $r = $r + 1;
}
print OUT "\n";
print OUT "Reverse oligos\n";
print "Reverse oligos\n";
$r = 1;
for ($i = $seqlen - $Overlap - $OL; $i >= 0; $i-=$OL)
{
     print OUT "\n";
     print "\n";
     $oligo = substr($revcomp,$i,$OL);
     print OUT "$oligname R- $r        $oligo";
     print "$oligname R- $r        $oligo";
     $r = $r + 1;
}
#Rectify and print out the last reverse oligo consisting of 1/2 from the beginning # of the reverse complement.
$oligo = substr($revcomp,1,$Overlap);
print OUT "$oligo\n";
print "$oligo\n";
#close files and exit
close (IN)     || die "can't close $a:$!";
close (OUT)    || die "can't close $b:$!";
print "\n";
print "\n";
print "Processing completed.\n";
```

-continued

The input file format is as follows:

print "\n";
print "\n";
print "Have a nice day!\n";

Assembly of Parsed Oligonucleotides Using a Two-Step PCR Reaction:

Obtain arrayed sets of parsed overlapping oligonucleotides, 50 bases each, with an overlap of about 25 base pairs (bp). The oligonucleotide concentration is from 250 nM (250 μM/ml). 50 base oligos give $T_m$s from 75 to 85 degrees C., 6 to 10 od$_{260}$, 11 to 15 nanomoles, 150 to 300 μg. Resuspend in 50 to 100 μl of $H_2O$ to make 250 nM/ml. Combine equal amounts of each oligonucleotide to final concentration of 250 μM (250 nM/ml). Add 1 μl of each to give 192 μl. Add 8 μl dH$_2$O to bring up to 200 μl. Final concentration is 250 μM mixed oligos. Dilute 250-fold by taking 10 μl of mixed oligos and add to 1 ml of water. (1/100; 2.5 mM) then take 1 μl of this and add to 24 μl 1×PCR mix. The PCR reaction includes:

| | |
|---|---|
| 10 mM | TRIS-HCl, pH 9.0 |
| 2.2 mM | MgCl$_2$ |
| 50 mM | KCl |
| 0.2 mM | each dNTP |
| 0.1% | Triton X-100 |

One U TaqI polymerase is added to the reaction. The reaction is thermoycled under the following conditions Following assembly amplification, take 2.5 μl of this assembly mix and add to 100 μl of PCR mix. (40×dilution). Prepare outside primers by taking 1 μl of F1 (forward primer) and 1 μl of R96 (reverse primer) at 250 μM (250 nm/ml–0.250 nmole/μl) and add to the 100 μl PCR reaction. This gives a final concentration of 2.5 μM each oligo. Add 1 U Taq1 polymerase and thermocycle under the following conditions:

35 cycles (or original protocol 23 cycles)

| | |
|---|---|
| 94 degrees | 30 s |
| 50 degrees | 30 s |
| 72 degrees | 60 s |

Extract with phenol/chloroform. Precipitate with ethanol. Resuspend in 10 μl of dH$_2$O and analyze on an agarose gel.

Assembly of Parsed Oligonucleotides Using Taq1 Ligation

Arrayed sets of parsed overlapping oligonucleotides of about 25 to 150 bases in length each, with an overlap of about 12 to 75 base pairs (bp), are obtained. The oligonucleotide concentration is from 250 nM (250 μM/ml). For example, 50 base oligos give $T_m$s from 75 to 85 degrees C., 6 to 10 od$_{260}$, 11 to 15 nanomoles, 150 to 300 μg. Resuspend in 50 to 100 ml of $H_2O$ to make 250 nM/ml.

Using a robotic workstation, equal amounts of forward and reverse oligos are combined pairwise. Take 10 μl of forward and 10 al of reverse oligo and mix in a new 96-well v-bottom plate. This gives one array with sets of duplex oligonucleotides at 250 μM, according to pooling scheme Step 1 in Table 1. Prepare an assembly plate by taking 2 μl of each oligomer pair and adding to a fresh plate containing 100 μl of ligation mix in each well. This gives an effective concentration of 2.5 μM or 2.5 nM/ml. Transfer 20 μl of each well to a fresh microwell plate and add 1 μl of T4 polynucleotide kinase and 1 μl of 1 mM ATP to each well. Each reaction will have 50 pmoles of oligonucleotide and 1 nmole ATP. Incubate at 37 degrees C. for 30 minutes.

Initiate assembly according to Steps 2–7 of Table 1. Carry out pooling Step 2 mixing each successive well with the next. Add 1 μl of Taq1 ligase to each mixed well. Cycle once at 94 degrees for 30 sec; 52 degrees for 30s; then 72 degrees for 10 minutes.

Carry out step 3 (Table 1) of pooling scheme and cycle according to the temperature scheme above. Carry out steps 4 and 5 of the pooling scheme and cycle according to the temperature scheme above. Carry out pooling scheme step 6 and take 10 μl of each mix into a fresh microwell. Carry out step 7 pooling scheme by pooling the remaining three wells. Reaction volumes will be:

| | |
|---|---|
| Initial plate has 20 ul per well. | |
| Step 2 | 20 ul + 20 ul = 40 ul |
| Step 3 | 80 ul |
| Step 4 | 160 ul |
| Step 5 | 230 ul |
| Step 6 | 10 ul + 10 ul = 20 ul |
| Step 7 | 20 + 20 + 20 = 60 ul final reaction volume |

A final PCR amplification was then performed by taking 2 ul of final ligation mix and add to 20 ul of PCR mix containing 10 mM TRIS-HCl, pH 9.0, 2.2 mM MgCl$_2$, 50 mM KCl, 0.2 mM each dNTP and 0.1% Triton X-100

Prepare outside primers by taking 1 μl of F1 (forward primer) and 1 μl of R96 (reverse primer) at 250 μM (250 nm/ml–0.250 nmole/μl) and add to the 100 μl PCR reaction giving a final concentration of 2.5 uM each oligo. Add 1 U Taq1 polymerase and cycle for 35 cycles under the following conditions: 94 degrees for 30s; 50 degrees for 30s; and 72 degrees for 60s. Extract the mixture with phenol/chloroform. Precipitate with ethanol. Resuspend in 10 μl of dH$_2$O and analyze on an agarose gel.

TABLE 1

Pooling scheme for ligation assembly.
Ligation method - Well pooling scheme

| STEP | FROM | TO |
|---|---|---|
| 1 | All F | All R |
| 2 | A1 | A2 |
| | A3 | A4 |
| | A5 | A6 |
| | A7 | A8 |
| | A9 | A10 |
| | A11 | A12 |
| | B1 | B2 |
| | B3 | B4 |
| | B5 | B6 |
| | B7 | B8 |
| | B9 | B10 |
| | B11 | B12 |
| | C1 | C2 |
| | C3 | C4 |
| | C5 | C6 |
| | C7 | C8 |
| | C9 | C10 |
| | C11 | C12 |
| | D1 | D2 |
| | D3 | D4 |
| | D5 | D6 |
| | D7 | D8 |
| | D9 | D10 |
| | D11 | D12 |
| | E1 | E2 |
| | E3 | E4 |

TABLE 1-continued

Pooling scheme for ligation assembly.
Ligation method - Well pooling scheme

| STEP | FROM | TO |
|---|---|---|
|  | E5 | E6 |
|  | E7 | E8 |
|  | E9 | E10 |
|  | E11 | E12 |
|  | F1 | F2 |
|  | F3 | F4 |
|  | F5 | F6 |
|  | F7 | F8 |
|  | F9 | F10 |
|  | F11 | F12 |
|  | G1 | G2 |
|  | G3 | G4 |
|  | G5 | G6 |
|  | G7 | G8 |
|  | G9 | G10 |
|  | G11 | G12 |
|  | H1 | H2 |
|  | H3 | H4 |
|  | H5 | H6 |
|  | H7 | H8 |
|  | H9 | H10 |
|  | H11 | H12 |
| 3 | A2 | A4 |
|  | A6 | A8 |
|  | A10 | A12 |
|  | B2 | B4 |
|  | B6 | B8 |
|  | B10 | B12 |
|  | C2 | C4 |
|  | C6 | C8 |
|  | C10 | C12 |
|  | D2 | D4 |
|  | D6 | D8 |
|  | D10 | D12 |
|  | E2 | E4 |
|  | E6 | E8 |
|  | E10 | E12 |
|  | F2 | F4 |
|  | F6 | F8 |
|  | F10 | F12 |
|  | G2 | G4 |
|  | G6 | G8 |
|  | G10 | G12 |
|  | H2 | H4 |
|  | H6 | H8 |
|  | H10 | H12 |
| 4 | A4 | A8 |
|  | A12 | B4 |
|  | B8 | B12 |
|  | C4 | C8 |
|  | C12 | D4 |
|  | D8 | D12 |
|  | E4 | E8 |
|  | E12 | F4 |
|  | F8 | F12 |
|  | G4 | G8 |
|  | G12 | H4 |
|  | H8 | H12 |
| 5 | A8 | B4 |
|  | B12 | C8 |
|  | D4 | D12 |
|  | E8 | F4 |
|  | F12 | G8 |
|  | H4 | H12 |
| 6 | B4 | C8 |
|  | D12 | F4 |
|  | GB | H12 |
| 7 | C8 | F4 |

Assembly of Parsed oligonucleotides Using Taq I Synthesis and Assembly

Arrayed sets of parsed overlapping oligonucleotides of about 25 to 150 bases in length each, with an overlap of about 12 to 75 base pairs (bp), are obtained. The oligonucleotide concentration is from 250 nM (250 $\mu$M/ml). 50 base oligos give $T_m$s from 75 to 85 degrees C., 6 to 10 $od_{260}$, 11 to 15 nanomoles, 150 to 300 $\mu$g. Resuspend in 50 to 100 ml of H$_2$O to make 250 nM/ml.

The invention envisions using a robotic workstation to accomplish nucleic acid assembly. In the present example, two working plates containing forward and reverse oligonucleotides in a PCR mix at 2.5 mM are prepared and 1 $\mu$l of each oligo are added to 100 $\mu$l of PCR mix in a fresh microwell providing one plate of forward and one of reverse oligos in an array. Cycling assembly is then initiated as follows according to the pooling scheme outlined in Table 1. In the present example, 96 cycles of assembly can be accomplished according to this scheme.

Remove 2 $\mu$l of well F-E1 to a fresh well; remove 2 $\mu$l of R-E1 to a fresh well; add 18 $\mu$l of 1×PCR mix; add 1 U of Taq1 polymerase;

| Cycle once | 94 degrees | 30 s |
|---|---|---|
|  | 52 degrees | 30 s |
|  | 72 degrees | 30 s |

Subsequently, remove 2 $\mu$l of well F-E2 to the reaction vessel; remove 2 $\mu$l of well R-D12 to the reaction vessel. Cycle once according to the temperatures above. Repeat the pooling and cycling according to the scheme outlined in Table 1 for about 96 cycles.

A PCR amplification is then performed by taking 2 $\mu$l of final reaction mix and adding it to 20 $\mu$l of a PCR mix comprising:

| 10 mM | TRIS-HCl, pH 9.0 |
|---|---|
| 2.2 mM | MgCl2 |
| 50 mM | KCl |
| 0.2 mM | each dNTP |
| 0.1% | Triton X-100 |

Outside primers are prepared by taking 1 $\mu$l of F1 and 1 ml of R96 at 250 mM (250 nm/ml–0.250 nmole/ml) and add to the 100 $\mu$l PCR reaction. This gives a final concentration of 2.5 $\mu$M each oligo. 1 U Taq1 polymerase is subsequently added and the reaction is cycled for about 23 to 35 cycles under the following conditions:

| 94 degrees | 30 s |
|---|---|
| 50 degrees | 30 s |
| 72 degrees | 60 s |

The reaction is subsequently extracted with phenol/chloroform, precipitated with ethanol and resuspend in 10 ml of dH20 for analysis on an agarose gel.

Equal amounts of forward and reverse oligos pairwise are added by taking 10 $\mu$l of forward and 10 $\mu$l of reverse oligo and mix in a new 96-well v-bottom plate. This provides one array with sets of duplex oligonucleotides at 250 mM, according to pooling scheme Step 1 in Table 1. An assembly plate was prepared by taking 2 $\mu$l of each oligomer pair and adding them to the plate containing 100 $\mu$l of ligation mix in each well. This gives an effective concentration of 2.5 $\mu$M or 2.5 nM/ml. About 20 $\mu$l of each well is transferred to a fresh microwell plate in addition to 1 $\mu$l of T4 polynucleotide kinase and 1 $\mu$l of 1 mM ATP. Each reaction will have 50 pmoles of oligonucleotide and 1 nmole ATP. Incubate at 37 degrees for 30 minutes. Nucleic acid assembly was initiated according to Steps 2–7 of Table 1. Step 2 pooling is carried out by mixing each well with the next well in succession. 1 µl of Taq1 ligase to is added to each mixed well and cycled once as follows:

| 94 degrees | 30 sec |
| 52 degrees | 30 s |
| 72 degrees | 10 minutes |

Step 3 of pooling scheme is carried out and cycled according to the temperature scheme above. Steps 4 and 5 of the pooling scheme are carried out and cycled according to the temperature scheme above. Carry out pooling scheme step 6 and take 10 µl of each mix into a fresh microwell. Step 7 pooling scheme is carried out by pooling the remaining three wells. The reaction volumes will be (initial plate has 20 µl per well):

| Step 2 | 20 µl + 20 µl = 40 µl |
| Step 3 | 80 µl |
| Step 4 | 160 µl |
| Step 5 | 230 µl |
| Step 6 | 10 µl + 10 µl = 20 µml |
| Step 7 | 20 + 20 + 20 = 60 µl final reaction volume |

A final PCR amplification is performed by taking 2 µl of the final ligation mix and adding it to 20 µl of PCR mix comprising:

| 10 mM | TRIS-HCl, pH 9.0 |
| 2.2 mM | MgCl2 |
| 50 mM | KCl |
| 0.2 mM | each dNTP |
| 0.1% | Triton X-100 |

Outside primers are prepared by taking 1 µl of F1 and 1 µl of R96 at 250 mM (250 nm/ml–0.250 nmole/ml) and adding them to the 100 µl PCR reaction giving a final concentration of 2.5 uM for each oligo. Subsequently, 1 U of Taq1 polymerase is added and cycled for about 23 to 35 cycles under the following conditions:

| 94 degrees | 30 s |
| 50 degrees | 30 s |
| 72 degrees | 60 s |

The product is extracted with phenol/chloroform, precipitate with ethanol, resuspend in 10 µl of dH20 and analyzed on an agarose gel.

TABLE 2

Pooling scheme for assembly using Taq1 polymerase (also topoisomerase II).

| Step | Forward oligo | | | | Reverse oligo | | | |
|---|---|---|---|---|---|---|---|---|
| 1 | F | E | 1 | + | R | E | 1 | Pause |
| 2 | F | E | 2 | + | R | D | 12 | Pause |
| 3 | F | E | 3 | + | R | D | 11 | Pause |
| 4 | F | E | 4 | + | R | D | 10 | Pause |
| 5 | F | E | 5 | + | R | D | 9 | Pause |
| 6 | F | E | 6 | + | R | D | 8 | Pause |
| 7 | F | E | 7 | + | R | D | 7 | Pause |
| 8 | F | E | 8 | + | R | D | 6 | Pause |
| 9 | F | E | 9 | + | R | D | 5 | Pause |
| 10 | F | E | 10 | + | R | D | 4 | Pause |
| 11 | F | E | 11 | + | R | D | 3 | Pause |
| 12 | F | E | 12 | + | R | D | 2 | Pause |
| 13 | F | F | 1 | + | R | D | 1 | Pause |
| 14 | F | F | 2 | + | R | C | 12 | Pause |
| 15 | F | F | 3 | + | R | C | 11 | Pause |
| 16 | F | F | 4 | + | R | C | 10 | Pause |
| 17 | F | F | 5 | + | R | C | 9 | Pause |
| 18 | F | F | 6 | + | R | C | 8 | Pause |
| 19 | F | F | 7 | + | R | C | 7 | Pause |
| 20 | F | F | 8 | + | R | C | 6 | Pause |
| 21 | F | F | 9 | + | R | C | 5 | Pause |
| 22 | F | F | 10 | + | R | C | 4 | Pause |
| 23 | F | F | 11 | + | R | C | 3 | Pause |
| 24 | F | F | 12 | + | R | C | 2 | Pause |
| 25 | F | G | 1 | + | R | C | 1 | Pause |
| 26 | F | G | 2 | + | R | B | 12 | Pause |
| 27 | F | G | 3 | + | R | B | 11 | Pause |
| 28 | F | G | 4 | + | R | B | 10 | Pause |
| 29 | F | G | 5 | + | R | B | 9 | Pause |
| 30 | F | G | 6 | + | R | B | 8 | Pause |
| 31 | F | G | 7 | + | R | B | 7 | Pause |
| 32 | F | C | 8 | + | R | B | 6 | Pause |
| 33 | F | G | 9 | + | R | B | 5 | Pause |
| 34 | F | G | 10 | + | R | B | 4 | Pause |
| 35 | F | G | 11 | + | R | B | 3 | Pause |
| 36 | F | G | 12 | + | R | B | 2 | Pause |
| 37 | F | H | 1 | + | R | B | 1 | Pause |
| 38 | F | H | 2 | + | R | A | 12 | Pause |
| 39 | F | H | 3 | + | R | A | 11 | Pause |
| 40 | F | H | 4 | + | R | A | 10 | Pause |
| 41 | F | H | 5 | + | R | A | 9 | Pause |
| 42 | F | H | 6 | + | R | A | 8 | Pause |
| 43 | F | H | 7 | + | R | A | 7 | Pause |
| 44 | F | H | 8 | + | R | A | 6 | Pause |
| 45 | F | H | 9 | + | R | A | 5 | Pause |
| 46 | F | H | 10 | + | R | A | 4 | Pause |
| 47 | F | H | 11 | + | R | A | 3 | Pause |
| 48 | F | H | 12 | + | R | A | 2 | Pause |

TABLE 3

Alternate pooling scheme (initiating assembly from the 5' or 3' end)

| | | | |
|---|---|---|---|
| 1. | F-A1 | R-A1 | denature, anneal, polymerase extension |
| 2. | F-A2 | R-H12 | denature, anneal, polymerase extension |
| 3. | F-A3 | R-H11 | denature, anneal, polymerase extension |
| 4. | F-A4 | R-H10 | denature, anneal, polymerase extension |
| 5. | F-A5 | R-H9 | denature, anneal, polymerase extension |
| 6. | F-A6 | R-H8 | denature, anneal, polymerase extension |
| 7. | F-A7 | R-H7 | denature, anneal, polymerase extension |
| 8. | F-A8 | R-H6 | denature, anneal, polymerase extension |
| 9. | F-A9 | R-H5 | denature, anneal, polymerase extension |
| 10. | F-A10 | R-H4 | denature, anneal, polymerase extension |
| 11. | F-A11 | R-H3 | denature, anneal, polymerase extension |
| 12. | F-A12 | R-H2 | denature, anneal, polymerase extension |
| 13. | F-B1 | R-H1 | denature, anneal, polymerase extension |
| 14. | F-B2 | R-G12 | denature, anneal, polymerase extension |
| 15. | F-B3 | R-G11 | denature, anneal, polymerase extension |
| 16. | F-B4 | R-G10 | denature, anneal, polymerase extension |
| 17. | F-B5 | R-G9 | denature, anneal, polymerase extension |
| 18. | F-B6 | R-G8 | denature, anneal, polymerase extension |
| 19. | F-B7 | R-G7 | denature, anneal, polymerase extension |
| 20. | F-B8 | R-G6 | denature, anneal, polymerase extension |
| 21. | F-B9 | R-G5 | denature, anneal, polymerase extension |
| 22. | F-B10 | R-G4 | denature, anneal, polymerase extension |
| 23. | F-B11 | R-G3 | denature, anneal, polymerase extension |
| 24. | F-B12 | R-G2 | denature, anneal, polymerase extension |

TABLE 3-continued

Alternate pooling scheme (initiating assembly from the 5' or 3' end)

| | | | |
|---|---|---|---|
| 25. | F-C1 | R-G1 | denature, anneal, polymerase extension |
| 26. | F-C2 | R-F12 | denature, anneal, polymerase extension |
| 27. | F-C3 | R-F11 | denature, anneal, polymerase extension |
| 28. | F-C4 | R-F10 | denature, anneal, polymerase extension |
| 29. | F-C5 | R-F9 | denature, anneal, polymerase extension |
| 30. | F-C6 | R-F8 | denature, anneal, polymerase extension |
| 31. | F-C7 | R-F7 | denature, anneal, polymerase extension |
| 32. | F-C8 | R-F6 | denature, anneal, polymerase extension |
| 33. | F-C9 | R-F5 | denature, anneal, polymerase extension |
| 34. | F-C10 | R-F4 | denature, anneal, polymerase extension |
| 35. | F-C11 | R-F3 | denature, anneal, polymerase extension |
| 36. | F-C12 | R-F2 | denature, anneal, polymerase extension |
| 37. | F-D1 | R-F1 | denature, anneal, polymerase extension |
| 38. | F-D2 | R-E12 | denature, anneal, polymerase extension |
| 39. | F-D3 | R-E11 | denature, anneal, polymerase extension |
| 40. | F-D4 | R-E10 | denature, anneal, polymerase extension |
| 41. | F-D5 | R-E9 | denature, anneal, polymerase extension |
| 42. | F-D6 | R-E8 | denature, anneal, polymerase extension |
| 43. | F-D7 | R-E7 | denature, anneal, polymerase extension |
| 44. | F-D8 | R-E6 | denature, anneal, polymerase extension |
| 45. | F-D9 | R-E5 | denature, anneal, polymerase extension |
| 46. | F-D10 | R-E4 | denature, anneal, polymerase extension |
| 47. | F-D11 | R-E3 | denature, anneal, polymerase extension |
| 48. | F-D12 | R-E2 | denature, anneal, polymerase extension |
| 49. | F-E1 | R-E1 | denature, anneal, polymerase extension |
| 50. | F-E2 | R-D12 | denature, anneal, polymerase extension |
| 51. | F-E3 | R-D11 | denature, anneal, polymerase extension |
| 52. | F-E4 | R-D10 | denature, anneal, polymerase extension |
| 53. | F-E5 | R-D9 | denature, anneal, polymerase extension |
| 54. | F-E6 | R-D8 | denature, anneal, polymerase extension |
| 55. | F-E7 | R-D7 | denature, anneal, polymerase extension |
| 56. | F-E8 | R-D6 | denature, anneal, polymerase extension |
| 57. | F-E9 | R-D5 | denature, anneal, polymerase extension |
| 58. | F-E10 | R-D4 | denature, anneal, polymerase extension |
| 59. | F-E11 | R-D3 | denature, anneal, polymerase extension |
| 60. | F-E12 | R-D2 | denature, anneal, polymerase extension |
| 61. | F-F1 | R-D1 | denature, anneal, polymerase extension |
| 62. | F-F2 | R-C12 | denature, anneal, polymerase extension |
| 63. | F-F3 | R-C11 | denature, anneal, polymerase extension |
| 64. | F-F4 | R-C10 | denature, anneal, polymerase extension |
| 65. | F-F5 | R-C9 | denature, anneal, polymerase extension |
| 66. | F-F6 | R-C8 | denature, anneal, polymerase extension |
| 67. | F-F7 | R-C7 | denature, anneal, polymerase extension |
| 68. | F-F8 | R-C6 | denature, anneal, polymerase extension |
| 69. | F-F9 | R-C5 | denature, anneal, polymerase extension |
| 70. | F-F10 | R-C4 | denature, anneal, polymerase extension |
| 71. | F-F11 | R-C3 | denature, anneal, polymerase extension |
| 72. | F-F12 | R-C2 | denature, anneal, polymerase extension |
| 73. | F-G1 | R-C1 | denature, anneal, polymerase extension |
| 74. | F-G2 | R-B12 | denature, anneal, polymerase extension |
| 75. | F-G3 | R-B11 | denature, anneal, polymerase extension |
| 76. | F-G4 | R-B10 | denature, anneal, polymerase extension |
| 77. | F-G5 | R-B9 | denature, anneal, polymerase extension |
| 78. | F-G6 | R-B8 | denature, anneal, polymerase extension |
| 79. | F-G7 | R-B7 | denature, anneal, polymerase extension |
| 80. | F-G8 | R-B6 | denature, anneal, polymerase extension |
| 81. | F-G9 | R-B5 | denature, anneal, polymerase extension |
| 82. | F-G10 | R-B4 | denature, anneal, polymerase extension |
| 83. | F-G11 | R-B3 | denature, anneal, polymerase extension |
| 84. | F-G12 | R-B2 | denature, anneal, polymerase extension |
| 85. | F-H1 | R-B1 | denature, anneal, polymerase extension |
| 86. | F-H2 | R-A12 | denature, anneal, polymerase extension |
| 87. | F-H3 | R-A11 | denature, anneal, polymerase extension |
| 88. | F-H4 | R-A10 | denature, anneal, polymerase extension |
| 89. | F-H5 | R-A9 | denature, anneal, polymerase extension |
| 90. | F-H6 | R-A8 | denature, anneal, polymerase extension |
| 91. | F-H7 | R-A7 | denature, anneal, polymerase extension |
| 92. | F-H8 | R-A6 | denature, anneal, polymerase extension |
| 93. | F-H9 | R-A5 | denature, anneal, polymerase extension |
| 94. | F-H10 | R-A4 | denature, anneal, polymerase extension |
| 95. | F-H11 | R-A3 | denature, anneal, polymerase extension |
| 96. | F-H12 | R-A2 | denature, anneal, polymerase extension |

Assembly of Nucleic Acid Molecules

The nucleic acid molecules listed in Table 4 have been produced using the methods described herein. The features and characteristics of each nucleic acid molecule is also described in Table 4.

As described in Table 4, a synthetic plasmid of 4800 bp in length was assembled. The plasmid comprises 192 oligonucleotides (two sets of 96 overlapping 50 mers; 25 bp overlap). The plasmid is essentially pUC containing kanamycin resistance instead of ampicillin resistance. The synthetic plasmid also contains lux A and B genes from the *Vibrio fisheri* bacterial luciferase gene. The SynPucl9 plasmid is 2700 bp in length comprising a sequence essentially identical to pUC19 only shortened to precisely 2700 bp. Two sets of 96 50 mers were used to assemble the plasmid. The Synlux4 pUC19 plasmid was shortened and luxA gene was added. 54 100-mer oligonucleotides comprising two sets of 27 oligonucleotides were used to assemble the plasmid. The miniQE10 plasmid comprising 2400 bp was assembled using 48 50 mer oligonucleotides. MiniQE10 is an expression plasmid containing a 6×His tag and bacterial promoter for high-level polypeptide expression. MiniQE10 was assembled and synthesized using the Taq1 polymerase amplification method of the invention. The microQE plasmid is a minimal plasmid containing only an ampicillin gene, an origin of replication and a linker of pQE plasmids. MicroQE was assembled using either combinatoric ligation with 24 50-mers or with one tube PCR amplification. The SynFib1, SynFibB and SynFibG nucleic acid sequences are synthetic human fibrinogens manufactured using *E. coli* codons to optimize expression in a prokaryotic expression system.

TABLE 4

Synthetic nucleic acid molecules produced using the methods of the invention.

| | | | | | |
|---|---|---|---|---|---|
| Synthetic Plasmid | 4800 | 192 | 50 | circular | F1-F96 |
| SynPUC/19 | 2700 | 192 | 50 | circular | E01-F96 |
| SynLux/4 | 2700 | 54 | 100 | circular | F1-27 |
| MiniQE10 | 2400 | 48 | 50 | circular | |
| MicroQE | 1200 | 24 | 50 | circular | MQEF-1,24 |
| Synfib1 | 1850 | 75 | 50 | linear | SFAF1-37 |
| pQE25 | 2400 | 96 | 25 | circular | F1-F48 |
| SynFibB | 1500 | 60 | 59 | 50 mers linear | FibbF1-30 |
| | | | 1 | 25 mer | |
| SynFibG | 1350 | 54 | 53 | 50 mers linear | FibgF1-27 |
| | | | 1 | 25 mer | |

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of assembling a double-stranded polynucleotide comprising:
   (a) selecting a partially double-stranded initiating oligonucleotide, wherein said initiating oligonucleotide comprises a at least one overhang;
   (b) contacting said partially double-stranded initiating oligonucleotide with a next most terminal double-stranded oligonucleotide, wherein said next most terminal double-stranded oligonucleotide is contiguous with the initiating oligonucleotide and comprises at least one overhang, and wherein at least one overhang of said next most terminal double-stranded oligonucleotide is complementary to at least one overhang of said initiating oligonucleotide;
   (c) repeating (b) to sequentially add the next most terminal double-stranded oligonucleotide to the extended initiating oligonucleotide, whereby said double-stranded polynucleotide is synthesized.

2. The method of 1, wherein said initiating oligonucleotide in step (a) has a 3' and a 5' overhang.

3. The method of claim 1, wherein said next most terminal oligonucleotide has a 3' and a 5' overhang.

4. A method of assembling a target polynucleotide comprising:
   (a) providing a target polynucleotide sequence;
   (b) identifying at least one partially double-stranded initiating oligonucleotide present in said target polynucleotide, wherein said initiating oligonucleotide comprises a 5' overhang and a 3' overhang;
   (c) identifying a next most terminal double-stranded oligonucleotide present in said target polynucleotide, wherein said next most terminal double-stranded oligonucleotide is contiguous with the initiating oligonucleotide and comprises a 5' overhang and a 3' overhang, wherein at least one overhang of said next most terminal double-stranded oligonucleotide is complementary to at least one overhang of said initiating oligonucleotide;

(d) contacting said initiating oligonucleotide with said next most terminal double-stranded oligonucleotide under such conditions and for such time suitable for annealing, wherein said initiating sequence is extended; and (e) repeating (a) through (d) to sequentially add the next most terminal double-stranded oligonucleotide to the extended initiating oligonucleotide, whereby a target polynucleotide is synthesized.

5. The method of claim 4, wherein said intiating oligonucleotide is extended in a bi-directional manner.

6. The method of claim 4, wherein said intiating oligonucleotide is extended in a uni-directional manner.

7. The method of claim 4, wherein said intiating oligonucleotide is the 5' most terminal oligonucleotide of said target polypeptide.

8. The method of claim 4, wherein said intiating oligonucleotide is the 3' most terminal oligonucleotide of said target polypeptide.

9. The method of claim 4, wherein the target polynucleotide comprises a sequence that encodes a target polypeptide.

10. The method of claim 9, wherein said target polypeptide is a protein.

11. The method of claim 10, wherein said protein is an enzyme.

12. The method of claim 4, wherein said initiating oligonucleotide comprises a sequence identified by a computer program.

13. The method of claim 12, wherein said computer program comprises an algorithm comprising the following steps:
(a) parsing a protein sequence codon by codon;
(b) providing a synthetic gene sequence using *E. coli* Type II codons;
(c) parse the sequence of step (b) Q oligomer by Q oligomer into Q length oligonucleotides with X overlap for forward set;
(d) parse sequence into Q length oligonucleotide form the reverse strand ovelapping by X nucleotides;
(e) determine sequence of REVERSE sequence end "suffer" fragments of Q/2 length; and
(f) synthesize sequence using array synthesizers.

14. The method of claim 4, wherein said complementary overhang of said next most terminal double-stranded oligonucleotide comprises about fifty percent of the length of the strand having said complementary overhang.

15. The method of claim 14, wherein said strand having said complementary overhang is about 15 to 1000 nucleotides in length.

16. The method of claim 15, wherein said strand having said complementary overhang is about 20 to 500 nucleotides in length.

17. The method of claim 16, wherein said strand having said complementary overhang is about 25 to 100 nucleotides in length.

18. The method of claim 4, wherein the initiating oligonucleotide is attached to a solid support.

19. A method of assembling a double-stranded polynucleotide, comprising:
(a) chemically synthesizing a first set of oligonucleotides of at least 25 bases comprising a first strand of a double-stranded polynucleotide;
(b) chemically synthesizing a second set of oligonucleotides of at least 25 bases comprising a second complementary strand of said double-stranded polynucleotide, each of said oligonucleotides within said second set of said oligonucleotides overlapping with at least one oligonucleotide within said first set of said oligonucleotides; and
(c) annealing said first and second sets of oligonucleotides to produce a double-stranded polynucleotide in the absence of enzymatic synthesis.

20. The method of claim 19, wherein said double-stranded polynucleotide is at least 700 base pairs in length.

21. The method of claim 20, wherein said double-stranded polynucleotide is replication-competent.

22. A method of assembling a double-stranded polynucleotide, comprising:
(a) chemically synthesizing a first set of oligonucleotides comprising a first strand of a double-stranded polynucleotide;
(b) chemically synthesizing a second set of oligonucleotides comprising a second complementary strand of said double-stranded polynucleotide, each of said oligonucleotides within said second set of said oligonucleotides overlapping with at least one oligonucleotide within said first set of said oligonucleotides; and
(c) annealing in the presence of MutS protein said first and second sets of oligonucleotides to assemble a double-stranded polynucleotide.

23. A method of assembling a double-stranded polynucleotide comprising:
(a) chemically synthesizing a first set of oligonucleotides comprising a first strand of a double-stranded polynucleotide;
(b) chemically synthesizing a second set of oligonucleotides comprising a second complementary strand of said double-stranded polynucleotide, each of said oligonucleotides within said second set of said oligonucleotides overlapping with at least one oligonucleotide within said first set of said oligonucleotides, and
(c) annealing said first and second sets of oligonucleotides to produce a partially double-stranded component polynucleotide;
(d) repeating steps (a) through (c) to prepare a series of partially double-stranded component polynucleotides;
(e) selecting at least one partially double-stranded component polynucleotide present in said target polynucleotide to serve as the initiating polynucleotide, wherein said initiating polynucleotide comprises a 5' overhang and a 3' overhang;
(f) adding the next most terminal component polynucleotide, wherein said next most terminal component polynucleotide comprises at least one overhang that is complementary to at least one overhang of the initiating polynucleotide;
(g) contacting said initiating polynucleotide with said next most terminal component polynucleotide under such conditions and for such time suitable for annealing; and
(h) optionally repeating (e) through (g) to sequentially add said next most terminal component polynucleotide to the extended initiating polynucleotide, whereby a target polynucleotide is assembled in the absence of enzymatic polymerization.

* * * * *